United States Patent
Werner et al.

(10) Patent No.: US 7,632,981 B2
(45) Date of Patent: Dec. 15, 2009

(54) PROCESS OF PRODUCING ENVIRONMENTALLY SAFE TRANSGENIC ORGANISMS

(75) Inventors: Stefan Werner, Halle/Saale (DE); Sylvestre Marillonnet, Halle/Saale (DE); Victor Klimyuk, Halle/Saale (DE); Yuri Gleba, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 145 days.

(21) Appl. No.: 10/512,879

(22) PCT Filed: Apr. 29, 2002

(86) PCT No.: PCT/EP02/04724

§ 371 (c)(1),
(2), (4) Date: Oct. 28, 2004

(87) PCT Pub. No.: WO02/096192

PCT Pub. Date: Dec. 5, 2002

(65) Prior Publication Data

US 2006/0174365 A1    Aug. 3, 2006

(51) Int. Cl.
*C12N 15/82* (2006.01)
*C12N 15/84* (2006.01)
*C12N 15/83* (2006.01)
*C12N 15/62* (2006.01)
*A01H 5/00* (2006.01)
*A01H 1/00* (2006.01)

(52) U.S. Cl. .................. 800/285; 800/275; 800/288; 800/294; 800/300; 800/302; 800/303; 435/69.8; 435/470

(58) Field of Classification Search .................. None
See application file for complete search history.

(56) References Cited

U.S. PATENT DOCUMENTS

| | | | | |
|---|---|---|---|---|
| 6,015,794 | A * | 1/2000 | Haseloff et al. | 514/44 |
| 6,392,119 | B1 * | 5/2002 | Gutterson et al. | 800/278 |
| 6,852,911 | B1 * | 2/2005 | Izhar | 800/303 |
| 7,026,526 | B2 | 4/2006 | Snell | |

FOREIGN PATENT DOCUMENTS

| | | |
|---|---|---|
| WO | WO 92/13090 | 8/1992 |
| WO | WO 00/52146 | 9/2000 |
| WO | WO 00/71701 | 11/2000 |
| WO | WO 01/59091 A2 | 8/2001 |

OTHER PUBLICATIONS

Pelletier et al. Physiol. Veg. 22(3): 377-399 (1984).*
McCreath et al. Nature 405: 1066-1069+1 (Erratum) (Jul. 2000).*
Ayre, B., et al., "Design of Highly Specific Cytotoxins by Using Trans-splicing Ribozymes," *Proc. Natl. Acad. Sci. USA*, 1999, pp. 3507-3512, vol. 96, Applied Biological Sciences.
Puttaraju, M., et al., "Spliceosome-mediated RNA *trans*-splicing as a Tool for Gene Therapy," *Nature Biotechnology*, 1999, pp. 246-252, vol. 17.
Burgess, D., et al., "A novel, two-component system for cell lethality and its use in engineering nuclear male-sterility in plants," *The Plant Journal*, 2002, pp. 113-125, vol. 31(1).
Chen, L., et al., "Herbicide resistance from a divided EPSPS protein: the split *Synechocystis* DnaE intein as an in vivo affinity doman," *Gene*, 2001, pp. 39-48, vol. 263(1-2).
Gils, M., et al., "A novel hybrid seed system for plants," *Plant Biotechnology Journal*, 2008, pp. 226-235, vol. 6(3).
Goldman, M.H.S., et al., "Female sterile tobacco plants are produced by stigma-specific cell ablation," *The EMBO Journal*, 1994, pp. 2976-2984, vol. 13(13).
Kandasamy, M., et al., "Ablation of Papillar Cell Function in Brassica Flowers Results in the Loss of Stigma Receptivity to Pollination," *The Plant Cell*, 1993, pp. 263-275, vol. 5(3).
Pelletier, G., et al., "Plant protoplast fusion and somatic plant cell genetics," *Physiol. Veg.*, 1984, pp. 377-399, vol. 22(3).
Sessa, G., et al., "The expression of an abundant transmitting tract-specific endoglucanase (Sp41) is promoter-dependent and not essential for the reproductive physiology of tobacco," *Plant Molecular Biology*, 1995, pp. 969-982, vol. 29.
Sun, L., et al., "Protein *trans*-Splicing To Produce Herbicide-Resistant Acetolactate Synthase," *Applied and Environmental Microbiology*, 2001, pp. 1025-1029, vol. 67(3).
Thomson, J., et al., "Artificial Gene-clusters Engineering into Plants Using a Vector System Based on Intron- and Intein-Encoded Endonucleases," *In Vitro Cell. Dev. Biol.*, 2002, pp. 537-542, vol. 38, Society for In Vitro Biology.
Li, B., et al., "Human Acyl-CoA:Cholesterol Acyltransferase-1 (ACAT-1) Gene Organization and Evidence That the 4.3-Kilobase ACAT-1 mRNA Is Produced from Two Different Chromosomes," *The Journal of Biological Chemistry*, 1999, pp. 11060-11071, vol. 274(1).

\* cited by examiner

*Primary Examiner*—David T Fox
(74) *Attorney, Agent, or Firm*—Alston & Bird LLP

(57) ABSTRACT

A process of producing a transgenic multi-cellular plant or animal organism expressing a trait of interest and having a controlled distribution of said trait to progeny, wherein said process comprises hybridising a first multi-cellular organism or a cell thereof having a first heterologous DNA sequence comprising a first fragment of a nucleotide sequence encoding said trait of interest and a second multi-cellular organism or a cell thereof having a second heterologous DNA sequence comprising a second fragment of the nucleotide sequence encoding said trait of interest, whereby said first and said second heterologous sequences are designed such that said trait of interest arises due to RNA trans-splicing after said hybridation.

20 Claims, 9 Drawing Sheets

SEQUENCE LISTING

<160> NUMBER OF SEQ ID NOS: 17

<210> SEQ ID NO 1
<211> LENGTH: 300
<212> TYPE: DNA
<213> ORGANISM: Escherichia coli

<400> SEQUENCE: 1

```
attgctgatc cccatgtgta tcactggcaa actgtgatgg acgacaccgt cagtgcgtcc        60
gtcgcgcagg ctctcgatga gctgatgctt tgggccgagg actgccccga agtccggcac       120
ctcgtgcacg cggatttcgg ctccaacaat gtcctgacgg acaatggccg cataacagcg       180
gtcattgact ggagcgaggc gatgttcggg gattcccaat acgaggtcgc caacatcctc       240
ttctggaggc cgtggttggc ttgtatggag cagcagacgc gctacttcga gcggaggcat       300
```

<210> SEQ ID NO 2
<211> LENGTH: 42
<212> TYPE: DNA
<213> ORGANISM: Artificial Sequence
<220> FEATURE:
<223> OTHER INFORMATION: primer Targhpt1

<400> SEQUENCE: 2
atgcctcgag ttactagaat tgctgatccc catgtgtatc ac    42

<210> SEQ ID NO 3
<211> LENGTH: 34
<212> TYPE: DNA
<213> ORGANISM: Artificial Sequence
<220> FEATURE:
<223> OTHER INFORMATION: PCR primer

<400> SEQUENCE: 3
tcaggtcgac atgcctccgc tcgaagtagc gcgt    34

<210> SEQ ID NO 4
<211> LENGTH: 34
<212> TYPE: DNA
<213> ORGANISM: Artificial Sequence
<220> FEATURE:
<223> OTHER INFORMATION: PCR primer

<400> SEQUENCE: 4
tgactctaga attgctgatc cccatgtgta tcac    34

<210> SEQ ID NO 5
<211> LENGTH: 34
<212> TYPE: DNA
<213> ORGANISM: Artificial Sequence
<220> FEATURE:
<223> OTHER INFORMATION: PCR primer

<400> SEQUENCE: 5
tcagggtacc atgcctccgc tcgaagtagc gcgt    34

<210> SEQ ID NO 6
<211> LENGTH: 32
<212> TYPE: DNA
<213> ORGANISM: Artificial Sequence
<220> FEATURE:
<223> OTHER INFORMATION: PCR primer

<400> SEQUENCE: 6
ctagaattca tgagcggaga attaagggag tc    32

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
gtaactcgag tgacttcagc aggtgggtgt ag    32

<210> SEQ ID NO 8
<211> LENGTH: 32
<212> TYPE: DNA
<213> ORGANISM: Artificial Sequence
<220> FEATURE:
<223> OTHER INFORMATION: PCR primer

```
<400> SEQUENCE: 8
ggagaagctt ggcttcaaga gcgtggtcgc tg                                32

<210> SEQ ID NO 9
<211> LENGTH: 35
<212> TYPE: DNA
<213> ORGANISM: Artificial Sequence
<220> FEATURE:
<223> OTHER INFORMATION: PCR primer

<400> SEQUENCE: 9
catgccatgg tcaaatctcg gtgacgggca ggacc                             35

<210> SEQ ID NO 10
<211> LENGTH: 416
<212> TYPE: DNA
<213> ORGANISM: Tetrahymena thermophila

<400> SEQUENCE: 10
tctagactta tcgggtgaca aaagttatca ggcatgcacc tggtagctag tctttaaacc    60
aatagattgc atcggtttaa aaggcaagac cgtcaaattg cgggaagggg gtcaacagcc   120
gttcagtacc aagtctcagg ggaaactttg agatggcctt gcaaagggta tggtaataag   180
ctgacggaca tggtcctaac cacgcagcca agtcctaagt caacagatct tctgttgata   240
tggatgcagt tcacagacta aatgtcggtc ggggaagatg tattcttctc ataagatata   300
gtcggacctc tccttaatgg gagctagcgg atgaagtgat gcaacactgg agccgctggg   360
aactaatttg tatgcgaaag tatattgatt agttttggag tactcgtgat aagctt       416

<210> SEQ ID NO 11
<211> LENGTH: 180
<212> TYPE: DNA
<213> ORGANISM: Escherichia coli

<400> SEQUENCE: 11
ctgaactcac cgcgacgtct gtcgagaagt ttctgatcga aaagttcgac agcgtctccg    60
acctgatgca gctctcggag ggcgaagaat ctcgtgcttt cagcttcgat gtaggagggc   120
gtggatatgt cctgcgggta aatagctgcg ccgatggttt ctacaaagat cgttatgttt   180

<210> SEQ ID NO 12
<211> LENGTH: 41
<212> TYPE: DNA
<213> ORGANISM: Artificial Sequence
<220> FEATURE:
<223> OTHER INFORMATION: PCR primer

<400> SEQUENCE: 12
gcatctcgag ttactagact gaactcaccg cgacgtctgt c                      41

<210> SEQ ID NO 13
<211> LENGTH: 38
<212> TYPE: DNA
<213> ORGANISM: Artificial Sequence
<220> FEATURE:
<223> OTHER INFORMATION: PCR primer

<400> SEQUENCE: 13
ctgcggatcc aaaacataacg atcttgtaga aaccatcc                          38

<210> SEQ ID NO 14
```

-continued

```
<211> LENGTH: 1153
<212> TYPE: DNA
<213> ORGANISM: Artificial Sequence
<220> FEATURE:
<223> OTHER INFORMATION: 5' fragment of synthetic CryIIIA gene with 5'
      end or rice actin 1 intron flanked by Cla1 and Xho1 sites

<400> SEQUENCE: 14
atcgatgact gcagacaaca acaccgaagc cctcgacagt tctaccacta aggatgttat     60
ccagaagggt atctccgttg tgggagacct cttgggcgtg gttggatttc ccttcggtgg    120
agccctcgtg agcttctata caaactttct caacaccatt tggccaagcg aggacccttg    180
gaaagcattc atggagcaag ttgaagctct tatggatcag aagattgcag attatgccaa    240
gaacaaggct ttggcagaac tccagggcct tcagaacaat gtggaggact acgtgagtgc    300
attgtccagc tggcagaaga accctgttag ctccagaaat cctcacagcc aaggtaggat    360
cagagagttg ttctctcaag ccgaatccca cttcagaaat tccatgccta gctttgctat    420
ctccggttac gaggttcttt tcctcactac ctatgctcaa gctgccaaca cccacttgtt    480
tctccttaag gacgctcaaa tctatggaga agagtgggga tacgagaaag aggacattgc    540
tgagttctac aagcgtcaac ttaagctcac ccaagagtac actgaccatt gcgtgaaatg    600
gtataacgtt ggtctcgata agctcagagg ctcttcctac gagtcttggg tgaacttcaa    660
cagatacagg agagagatga ccttgactgt gctcgatctt atcgcactct ttcccttgta    720
cgatgtgaga ctctacccaa aggaagtgaa aactgagctt accagagacg tgctcactga    780
ccctattgtc ggagtcaaca accttagggg ttatggaact accttcagca atatcgaaaa    840
ctacattagg aaaccacatc tcttcgacta tcttcacaga attcaattcc acacaaggta    900
accaccccgc gtccctctcc tctttctttc tccgtttttt ttttccgtct cgtctcgatc    960
tttggccttg gtagtttggg ggcgagaggc ggcttcgtcg cccagatcgg tgcgcgggag   1020
gggcgggbam hatctcgcgg ctgggtctcg gcgtgcggcc ggatcctcgc ggggaatggg   1080
gctctcggat gtagatctga tccgccgttg ttgggggaga tgatggggcg tttaaaattt   1140
caagtcactc gag                                                       1153

<210> SEQ ID NO 15
<211> LENGTH: 1121
<212> TYPE: DNA
<213> ORGANISM: Artificial Sequence
<220> FEATURE:
<223> OTHER INFORMATION: 3' fragment of synthetic CryIIIA gene preceeded
      by 3' end of rice actin 1 intron flanked by HindIII and BamH1
      sites

<400> SEQUENCE: 15
aagcttgcca tgctaaacaa gatcaggaag aggggaaaag ggcactatgg tttatatttt     60
tatatatttc tgctgctgct cgtcaggctt agatgtgcta gatctttctt tcttcttttt    120
gtgggtagaa tttgaatccc tcagcattgt tcatcggtag tttttctttt catgatttgt    180
gacaaatgca gcctcgtgcg gagctttttt gtaggtttca accaggatac tatggtaacg    240
actccttcaa ctattggtcc ggtaactatg tttccaccag accaagcatt ggatctaatg    300
acatcatcac atctcccttc tatggtaaca agtccagtga acctgtgcag aaccttgagt    360
tcaacggcga gaaagtctat agagccgtcg caaacaccaa tctcgctgtg tggccatccg    420
cagtttactc aggcgtcaca aaggtggagt ttagtcagta taacgatcag accgatgagg    480
ccagcaccca gacttacgac tccaaacgta acgttggcgc agtctcttgg gattctatcg    540
```

-continued

```
accaattgcc tccagaaacc acagacgaac cattggagaa gggctacagc caccaactta        600
actatgtgat gtgcttcttg atgcaaggtt ccagagggac cattccagtg ttgacctgga        660
cacacaagtc cgtggacttc ttcaacatga tcgatagcaa gaagatcact caacttccct        720
tggtgaaagc ctacaagctg caatctggtg cttccgttgt cgcaggtccc agattcactg        780
gaggtgacat catccagtgc acagagaacg gcagcgcagc tactatctac gtgacacctg        840
atgtgtctta ctctcagaag tacagggcac gtattcatta cgcatctacc agccagatca        900
ccttcacact cagcttggat ggagcaccct tcaaccagta ttactttgac aagaccatca        960 acaaggtga cactctcaca tacaatagct tcaacttggc aagtttcagc acaccatttg       1020
aactctcagg caacaatctt cagatcggcg tcaccggtct cagcgccgga gacaaagtct      1080
acatcgacaa gattgagttc atcccagtga actgaggatc c                          1121

<210> SEQ ID NO 16
<211> LENGTH: 33
<212> TYPE: DNA
<213> ORGANISM: Artificial Sequence
<220> FEATURE:
<223> OTHER INFORMATION: PCR primer

<400> SEQUENCE: 16
gcatagatct ctgaactcac cgcgacgtct gtc                                      33

<210> SEQ ID NO 17
<211> LENGTH: 38
<212> TYPE: DNA
<213> ORGANISM: Artificial Sequence
<220> FEATURE:
<223> OTHER INFORMATION: PCR primer

<400> SEQUENCE: 17
ctgcgagctc aaacataacg atcttgtaga aaccatcc                                 38
```

PROCESS OF PRODUCING ENVIRONMENTALLY SAFE TRANSGENIC ORGANISMS

This application is the U.S. National Stage of International Application PCT/EP02/04724 filed Apr. 29, 2002, which designates the U.S. and was published by the International Bureau in English on Dec. 5, 2002, and which is hereby incorporated herein in its entirety by reference.

FIELD OF THE INVENTION

The present invention relates to a process of producing a transgenic multicellular plant or animal organism expressing a trait of interest and having a controlled distribution of said trait to progeny or to other organisms. The invention further relates to a multicellular plant or animal organism expressing a trait, whereby the distribution of said trait to progeny is controlled, i.e. the probability of transferring said trait to progeny, notably by cross-pollination, is very low. This inventions relates preferably to multi-cellular plants.

BACKGROUND OF THE INVENTION

The commercial use of genetically engineered crop species has caused concerns about the possible transfer of transgenes and traits encoded by transgenes from genetically modified plants (GM plants) into landraces, wild relatives or other non-GM plant varieties or related crop species (Ellstrand, N.C., 2001, *Plant Physiol.* 125, 1543-1545; Quist & Chapela, 2001, *Nature,* 414, 541-543), which could change the ecological balance in the affected ecosystems or lead to other, first of all, socioeconomic problems. Additionally, there is a certain fear that transgenes, especially antibiotic resistance genes used as transformation markers, can escape, through so-called horizontal transfer, into surrounding microorganisms (Chiter et al., 2000, *FEBS Lett.,* 481, 164-168), thus modifying the microflora in an undesirable way.

Although many of these worries are not well justified scientifically (Christou, P., 2002, *Transgenic Res.,* 11, iii-v), the creation of safe and controlled transgene management systems is highly desirable, as it might prevent potential problems in the future and shall help to protect the germplasm of existing plant species in the most efficient way. In addition, there are problems caused by contamination of organically grown crops or non-GM crops with transgenic cultivars. This has a serious impact on the marketing of transgenic as well as non-transgenic crops, an issue which cannot be ignored by producers.

Any transgenic material created by current technology and released into the environment has a potential of persisting there for a very long time. Common practice of plant genetic engineering is based on the use of expression cassettes and vectors that contain continuous coding sequence for the gene of interest. Such expression cassettes are integrated into a host chromosome and upon hybridization or another genetic information exchange between a GM plant and another organism, whether licit or illicit, the expression cassette is transmitted with a high probability to the progeny or another recipient as a functional transcriptional unit.

It is therefore an object of the invention to provide a process of producing a transgenic organism, notably plant organism, expressing a trait of interest, whereby distribution of said trait to progeny is controlled and occurs with low probability.

It is a further object of the invention to provide a controlled and biologically safe process of expressing a trait of interest in a multi-cellular organism or a cell thereof.

GENERAL DESCRIPTION OF THE INVENTION

The above objects are achieved by a process (i) of producing a transgenic multi-cellular plant or animal organism expressing a trait of interest and having a controlled distribution of said trait to progeny, wherein said process comprises hybridising a first multi-cellular organism or a cell thereof having a first heterologous DNA sequence comprising a first fragment of a sequence encoding said trait of interest and a second multi-cellular organism or a cell thereof having a second heterologous DNA sequence comprising a second fragment of the sequence encoding said trait of interest, whereby said first and said second heterologous sequences are designed such that said trait of interest arises due to RNA trans-splicing after said hybridisation. Production of transgenic multi-cellular plant organisms is preferred.

The above objects are further achieved by a process (ii) of producing a transgenic multi-cellular plant or animal organism expressing a trait of interest and having a controlled distribution to progeny and expression of said trait, said process comprising the provision of a multi-cellular organism or a cell thereof having a first heterologous DNA sequence comprising a first fragment of a sequence encoding said trait of interest; and the introduction of a second heterologous DNA (or RNA) sequence comprising a second fragment of the sequence encoding said trait of interest into a cell of said multi-cellular organism, whereby said first and said second heterologous sequences are designed such that the expression of said trait of interest arises due, to RNA trans-splicing after the cell has been switched by said introduction. Production of transgenic multi-cellular plant organisms is preferred.

Further, the invention provides transgenic organisms obtained or obtainable by one of the above processes.

The inventors of this invention have developed for the first time a method of rendering transgenic organisms environmentall safe in that the transgene or a trait of interest expressed by said organism has a controlled distribution to progeny of said organism. The invention solves a major problem of biotechnology, notably of plant biotechnology, since transfer of a transgene from a GM organism to other organisms can now be effectively controlled and limited. Transfer of a transgene to other organisms includes transfer to sexual progeny by cross-pollination as well as lateral gene transfer. The above processes make obtainable genetically modified multi-cellular organisms with a controlled containment of a trait of interest.

In both processes of the invention, the nucleotide sequence encoding or involved in said trait is split into two or more fragments. Preferably, said nucleotide sequence is split into two fragments. Said nucleotide sequence is typically a coding sequence (or an open reading frame) of an RNA or, preferably, of a protein involved in said trait. To obtain said fragments, said nucleotide sequence is preferably split such that each obtained fragment, upon expression, is incapable of generating said trait. Expression of said trait requires the presence of both said fragments in the same organism, notably in the same cells thereof, and linking by trans-splicing of said fragments. Herein, expression includes transcription, preferably expression includes transcription and translation. Each fragment preferably contains a sequence portion necessary for the function of the RNA or protein involved in said trait. For example, if said protein involved in said trait is an enzyme, each fragment preferably contains amino acids necessary for catalysis or substrate binding of the enzyme.

The following description focuses on the preferred embodiment, wherein said nucleotide sequence is split into two fragments. The first fragment is incorporated into a first heterologous sequence, the second fragment is incorporated into a second heterologous sequence, whereby at least said first heterologous sequence is a DNA sequence. In said process (i), both heterologous sequences are DNA sequences. In said process (ii), said first heterologous sequence is DNA, whereas said second heterologous sequence may be an RNA or a DNA sequence. Each heterologous sequence preferably contains, apart from said fragment, sequences required e.g. for transcription like a promoter and a transcription termination signal, or sequences required for translation.

Said first and/or said second heterologous sequence further contains or codes for a sequence capable of RNA trans-splicing with said second and/or said first heterologous sequence, respectively, for linking said first and said second fragment by trans-splicing. Said sequence capable of RNA trans-splicing may be a ribozyme (Rz) capable of trans-splicing. The trans-splicing ribozyme may be selected from the following group: group I intron-derived ribozymes, group II intron-derived ribozymes, and other natural or artificially designed ribozymes capable of specific RNA trans-splicing. Further, said trans-splicing may be spliceosome-mediated.

The process of the invention may also be used to assemble two or more traits by trans-splicing. This may be done as exemplified in example 1 and FIG. 5 by having 2 fragments involved in a trait (or involved a two traits) on each heterologous sequence.

Efficient trans-splicing of the first and the second heterologous sequences poses certain requirements to said heterologous sequences. Inter alia, homology of the P1 loop of the ribozyme to the 3' end of the 5' splicing fragment may lead to restrictions of the base sequence of the 5' splicing fragment. In order to avoid such restrictions, said first and/or said second heterologous sequence may contain an intron or a part thereof such that the RNA product of the trans-splicing reaction contains an intron capable of cis-splicing. Notably, sequences necessary for trans-splicing on the first and the second heterologous DNA sequences are incorporated in such a self-splicing intron. Said self-splicing intron may then be assembled in the trans-splicing reaction. Following trans-splicing, any non-desired sequences or sequences necessary for trans-splicing may be excised from the product of the trans-splicing reaction by cis-splicing (cf. FIG. 4). The design of cis-splicing introns is known in the art.

In process (i) of the invention, said first and said second heterologous DNA sequence are each incorporated in a multi-cellular organism or cells thereof according to methods generally known in the art. Preferably, at least one, more preferably both, of said heterologous sequences are stably incorporated into a chromosome of the nuclear genome of the organism. Said first and said second multi-cellular organisms obtained thereby are preferably made homozygous with respect to the respective heterologous DNA sequences according to procedures known in the art. Said first and said second multi-cellular organisms belong preferably to the same family, more preferably to the same genus, and most preferably to the same species of organisms.

Said first heterologous DNA sequence in said first multi-cellular organism and said second heterologous DNA sequence in said second multi-cellular organism may be incorporated into the same (homologous) or into different (non-homologous) chromosomes. It is preferred that they are incorporated into the same chromosome. Most preferably, they are incorporated into the same locus of the same chromosome. Methods for obtaining such relative locations of said first and said second heterologous sequences are known in the art. One possibility is to produce many transformants with each of said heterologous sequences. Then, the chromosome having said heterologous sequence incorporated as well as the location of the transformed sequence in the chromosome is determined by genetic or molecular biological methods. Then, a transformed multi-cellular organism having said heterologous sequence at a suitable location may be selected. This may be done with said first and said second multi-cellular organism, and a suitable pair of first and second organisms may be chosen. A further possibility is to use targeted integration into a desired locus of a particular chromosome making use of homologous recombination. Targeted integration may preferably be done using a multi-cellular plant having a targeting site pre-integrated into a chromosome in combination with site-specific recombination. The latter approach is particularly useful for introducing said first and said second heterologous sequence into the same locus of the same chromosome, as the same starting organism line having a pre-integrated targeting site may be used for transforming said heterologous sequences. Targeted integration is described e.g. in international patent application PCT/EP02/03266.

In process (i) of the invention, said first and said second multi-cellular organism or cells thereof are then hybridised for obtaining the transgenic multi-celllular plant or animal organism of the invention. Hybridising may be sexual crossing of organisms or fusion of cells of said organisms. Cell fusion may be fusion of germ cells or of somatic cells. If said organisms are plants, hybridising may involve pollination of plants or somatic cell fusion of protoplasts. Sexual crossing of plants is most preferred. Said hybridising brings said fragments encoding or being involved in said trait together in one organism such that said trait of interest arises due to RNA trans-splicing. Arising due to RNA trans-splicing means that trans-splicing is a necessary condition for the expression of said trait of interest. The production of the transgenic organism of the invention may comprise further steps in addition to said hybridising. In the case of plants, examples of such further steps include: growing and harvesting seeds, seeding, and growing the plant of the invention. In the case of protoplast fusion, such further steps include: propagating the fused protoplasts to obtain colonies, regeneration of plants.

Several relative locations of said first and said second heterologous sequences and the respective fragments exist in the transgenic multi-celllular plant or animal organism of the invention. Said first and said second heterologous sequences in said transgenic multi-cellular plant or animal should be positioned such that they segregate as unlinked loci. Said unlinked loci are preferably positioned so as to minimize recombination and creation of linkage between said loci. Said relative locations are generally shown in FIG. 2B using a diploid organism as an example.

In case I of FIG. 2B, said fragments are located on the same chromosome, i.e. they are physically linked on the same DNA molecule but are separated from each other by chromosome sequences native to the organism. The fragments will belong to different transcriptional units. Since crossing-over in meiosis may lead to separation of the fragments (or the heterologous sequences containing the fragments), the probability of transferring the trait encoded by both fragments to progeny is significantly reduced compared to the conventional case, where the trait is encoded by a continuous coding sequence.

In case II (see FIG. 2B), said first and said second fragment are located on different chromosomes (non-homologous chromosomes as opposed to allelic chromosomes). The frequency of inheriting said trait encoded by two fragments on different chromosomes upon self-crossing is about 50% and upon crossing with an organism not carrying any of these fragments 25%. Case II is preferred over case I.

In a more preferred case (case III in FIG. 2B), the two fragments are present on allelic (homologous) chromosomes. The closer the fragments are located, the lower the frequency of transferring the trait to progeny. In the most preferred case (case IV in FIG. 2B), the fragments are located in the same locus. Thus, the trait quickly segregates in cross-progeny of the multi-cellular plant or animal organism of the invention.

Controlled distribution of said trait to progeny means that the probability of transferring said trait to progeny is significantly reduced compared to conventional transgenic organisms that have a transgene involved in said trait encoded in one locus of a chromosome, notably as a single transcriptional unit. The frequency of appearance of said trait in progeny upon crossing said transgenic multi-cellular organism of the invention with an organism devoid of said first and said second heterologous sequences is less than 10%, preferably less than 1%, more preferably 0.1%, even more preferably less than 0.01%, an most preferably less than 0.001%. For comparison, the frequency of appearance of a transgene in progeny upon crossing a conventional transgenic (diploid) organism having said transgene in a single transcriptional unit and being heterozygous with respect to the transgene with another organism of the same species not having said transgene is about 50%.

In process (ii) of the invention, assembly of RNA involved in a trait of interest does not require hybridisation of organisms or cells. However, the specification given above for process (i) of the invention, also applies to process (ii) where applicable and unless specified differently. In this second process, said first heterologous sequence is typically DNA that is integrated into the nuclear genome of said multi-cellular organism. Said second heterologous sequence may be RNA or DNA. If it is DNA, sequences allowing transcription (e.g. a promoter functional in the organism) in said organism have to be provided with said second heterologous sequence for producing trans-splice able RNA. Said second heterologous sequence may be RNA, e.g. when viral infection based on an RNA virus is used. An RNA viral second heterologous RNA may however be introduced indirectly by introducing DNA transcribable to RNA.

Said second heterologous DNA or RNA sequence may or may not be incorporated into the nuclear genome of the multi-cellular organism. Preferably, it is not incorporated into the nuclear genome. This allows an extremely high degree of control of the distribution to progeny of the trait encoded in said first and second fragment.

The multi-cellular organism or cell thereof having a first heterologous DNA sequence may be provided as described for process (i). In contrast to process (i), the multi-cellular organism is preferably heterozygous with respect to the first heterologous sequence.

The introduction of said first and said second heterologous sequences may be a one-step or a two-step procedure. In the one-step procedure, said first and said second heterologous sequences are introduced into a multi-cellular organism together or at the same time and, preferably, by the same transformation method. Said first and said second heterologous sequences may e.g. be introduced as a mixture (e.g. a mixture of *Agrobacterium* strains each containing one of said heterologous sequences in T-DNA of Ti plasmids). In the two-step procedure, the multi-cellular organism or a cell thereof having the first heterologous DNA sequence is produced first, and said second heterologous sequence is introduced in an independent step. These two introductions may be performed by different transformation or transfection methods. Said introducing may be done by viral infection, *Agrobacterium*-mediated infection or non-biological transformation methods.

The processes of the invention, transgenic multi-cellular plant or animal organisms are produced. Multi-cellular plants are preferred. Among animals, mammals (e.g. mice, rats, rabbits, and animals used for human nutrition like pigs and bovine amimals) are preferred. Humans are excluded. Among plants, crop plants including barley, oat, rye, wheat, *zea mays*, rice, millet, potato, oilseed rape, canola, tomato, cotton, sorghum, and tobacco are preferred. The processes of the invention may be applied to diploid and to polyploid plants.

Examples for traits expressible according to the invention, notably in plants, are male sterility, herbicide resistance, insecticide resistance, a counter-selectable marker, organism morphology, seed content, seed stability, climate adaption, vitamine content, carbohydrate content and composition, fat content and composition etc. Further, said trait may be expression of a protein of interest, notably a pharmaceutical protein. Examples for such proteins are given below. In a preferred case (cf. example 1), two traits are expressed in a plant of the invention, e.g. a selectible marker gene and a gene of interest conferring a useful trait like insect resistance.

Said multi-cellular organisms and said transgenic multi-cellular organisms of the invention may be further genetically or transiently modified e.g. for providing functions necessary for said trans-splicing and/or said expressing of the trait of interest. Further, a second transgene involved in expression of said trait of interest or of a different trait may expressed.

The process of the invention may be used for a wide variety of applications. It may e.g. be used for expressing a trait of interest in said transgenic organism. Said trait may be any property of said organism, whether encoded by a single or by several genes. Said trait may be caused by expression of at least one RNA or, preferably, by the expression of at least one protein. Two or more RNAs and/or proteins may be necessary for said trait. In this case, it may be sufficient to control the expression of only one RNA or protein as described herein. It is, however, environmentally safer to control all the RNAs or proteins producing a trait by the processes of the invention (cf. example 1, FIG. 5).

The invention also allows to assemble sequence coding for a protein with modules of e.g. signal peptides, binding domains, retention signals, compartmentalisation signals, activation domains, domains with enzymatic activities, affinity tags, and regulatory sequences. Such a modular approach makes it simple to find an optimal expression cassette for a specific purpose or for finding an optimal secretory or transit peptide for a specific gene to be overexpressed and accumulated in the cell or a specific compartment thereof. It can be a valuable tool for functional genomics and proteomics studies. A library of plants may e.g. be created, whereby each member of the library contains a particular module (e.g. a specifec signal peptide) of one of the above module classes e.g. as said first fragment. The second fragment will then code for a protein of interest. Following said hybridising (process (i)) or said introduction (process (ii)), the coding RNA sequence of said protein is linked to said module by trans-splicing. It is preferred to carry out this modular approach with process (ii) of the invention and without stable integration of said second heterologous sequence into a chromosome.

In this invention, a trait may also be expressed in a transgenic multi-cellular organism by down-regulating a gene native to said organism. A gene may be down-regulated by any known methods, e.g. by anti-sense technology or by small interfering RNAs (siRNA). In such embodiments of the invention, an anti-sense RNA or a siRNA is provided by the product of the trans-splicing reaction, optionally after further processing like cis-splicing. A siRNA may be produced in the transgenic organism by designing said first and second heterologous sequences such that the product of trans-splicing comprises sequence portions having self-complementarity for forming a double-stranded RNA structure. Said double-stranded RNA structure may have a portion of sequence identity to a gene of the host cell and may be of sufficient length to inhibit expression of said gene in said cell. This method is particularly useful for functional genomics studies, notably in combination with the second process of the invention. The method of genetic inhibition by double-stranded RNA is generally described in WO 99/32619. An efficient method of down-regulating any desired target gene using small interfering RNAs is described in Brummelkamp et al. (Science 296, 550-553). These methods can easily be combined with the processes of the invention.

The most important application of process (i) is the production of hybrid seeds for generating plants for agricultural purposes or for protein production in said plants, whereby said plants have a controlled distribution of a trait to progeny. Said hybrid seeds allow the generation of plants expressing a trait of interest that is neither expressed in a parental line and quickly segregates in progeny.

The most important application of process (ii) is control of expression of a trait of interest. Expression of said trait may be triggered by introducing said second heterologous DNA sequence. If said second heterologous DNA sequence is incorporated into a nuclear chromosome, the same level of control of distribution of said trait is achievable as in process (i). If said second heterologous DNA sequence is not incorporated into a nuclear chromosome, the distribution of said trait is even further controlled, since transfer of said trait to progeny is extremely unlikely.

The invention further provides a transgenic multi-cellular plant or animal organism expressing a trait of interest, said organism having a controlled distribution of said trait to progeny, wherein expression of said trait involves production of an RNA molecule by trans-splicing of RNA fragments, whereby said RNA fragments are encoded or are located on different heterologous nucleotide molecules. Plant organisms are preferred. Said different heterologous nucleotide molecules may be on different chromosomes. Preferably, said RNA fragments are encoded on allelic chromosomes. Most preferably, said RNA fragments code, after trans-splicing, for a heterologous protein The invention further comprises parts or products of the transgenic organisms of the invention and plant seeds obtained by said hybridising.

DETAILED DESCRIPTION OF THE INVENTION

In this invnetion, we propose to split the coding sequence of a transgene involved in expression of a trait in two or more fragments capable of trans-splicing on the RNA level, and introduce these fragments into different chromosomes of the host genome, preferably in allelic chromosomes, of a transgenic multi-cellular organism. Once transcribed, these fragments can be assembled by RNA trans-splicing, thus forming functional RNA, notably mRNA, which can provide for the trait of interest. Since the breeding process usually involves very specific parental crosses, managing such two-allele system does not pose serious additional problems. Any undesired, spontaneous cross between the transgenic organism (notably a plant organism) of the invention and unwanted organisms effectively disassembles said trait, thus abolishing expression and greatly reducing the chance of functional gene transfer to illicit progeny.

The processes of the invention allow to build mechanisms, that would control either the expression of the transgene per se or it could be utilized to control the transgenic variety, as the progeny of any illicit cross is rendered non-viable. Both of these possibilities are inter alia contemplated in our invention.

The system of this invention also allows one skilled in the art to design schemes for selecting primary transformants based on a selectable marker that is effective and operable in the $T_0$ progeny, but alleles of which, upon subsequent crosses, segregate to different transgenic progeny and thus disappear as a functional selectable gene.

Furthermore, the invention allows rapid in vivo assembly of different genes by crossing parents that contain different fragments of a transcriptional unit of interest, thus allowing to swap different functional domains, such as translational enhancers, transit or signal or targeting peptides, purification tags, different functional domains of proteins, etc., by simply crossing plants carrying desired fragments of such a functional gene/transcriptional unit.

The RNA trans-splicing can be achieved by using engineered ribozymes. One of the early applications of the trans-splicing phenomenon was proposed by Sullenger and Cech (*Nature*, 1994, 371, 619-622,) who described experiments in which ribozyme-mediated trans-splicing is used to replace a defective portion of RNA with a functional structure by using a reengineered *Tetrahymena* group I intron to generate translatable lacZ transcripts in *E. coli*. They proposed trans-splicing as a general means of altering the sequence of specific host transcripts for the purposes of treatment of many genetic diseases.

Figure 1:
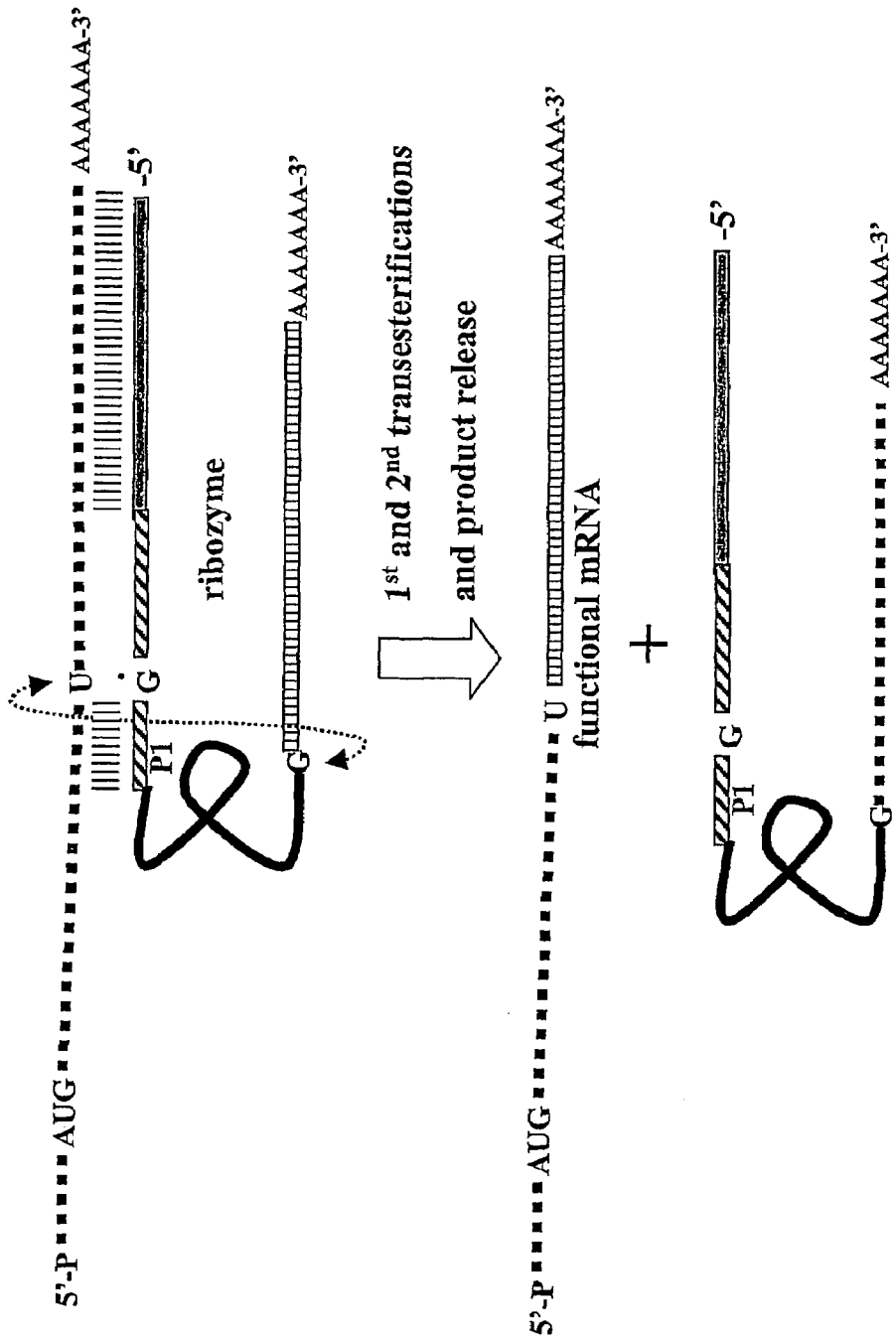
FIG. 1
General scheme of ribozyme-mediated trans-splicing resulting in functional mRNA formation.

Another use of trans-splicing was proposed by Ayre and colleagues (1999, *Proc. Natl. Acad. Sci. USA*, 96, 3507-3512) who developed a technology that utilizes ribozyme-mediated trans-splicing to target cytotoxins into cells in a highly specific manner. They used group I introns to splice the mRNA for Diphteria toxin A with virus mRNA to inactivate cells expressing viral mRNA, thus selectively inactivating infected yeast cells. The general principle of group 1 intron-derived ribozyme-mediated trans-splicing is shown in FIG. 1.

Yet another important application was developed by Mikheeva and Jarrell (1996, *Proc. Natl. Acad. Sci. USA*, 93 7486-7490) who used engineered group II introns to catalyze chimeric gene assembly. In this work, the ribozyme was modified so as to shuffle the mRNA of tissue plasminogen activator, and the resulting chimeric RNA was reversely transcribed into DNA. The approach allows to unidirectionally create libraries of genes that encode chimeric proteins with novel functions.

Figure 2A:
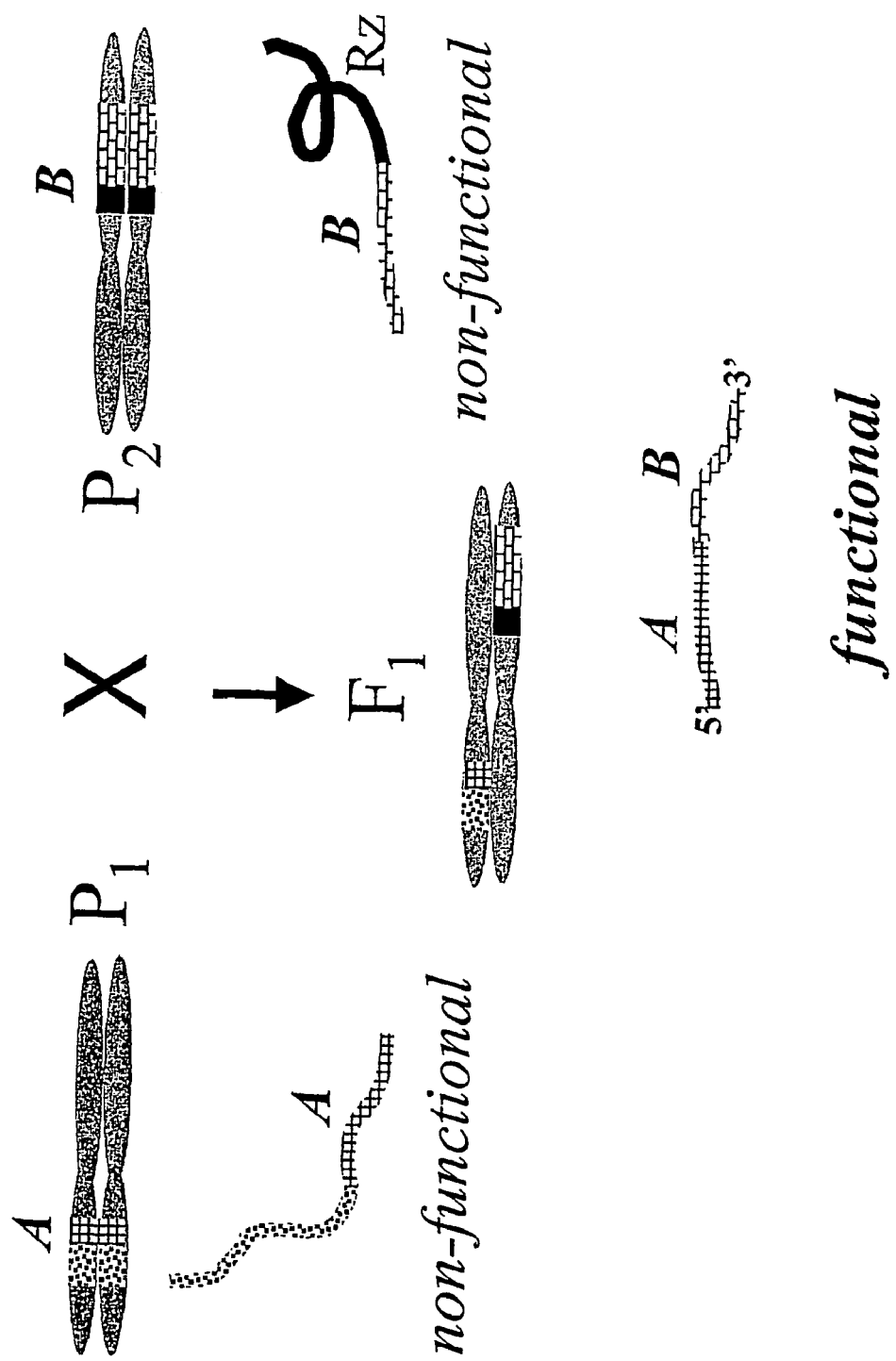
FIG. 2
A—depicts the general principle of the invention, where the trans-splicing—mediated formation of functional transcript takes place in cells of hybrid progeny;
B—depicts four possible relative locations of the first and the second heterologous DNA sequences on host chromosomes of the transgenic multi-cellular organism of the invention. A diploid organism having two chromosomes and a trait of interest encoded by two fragments (A and B) is used as an example.
C—depicts the basic principle of achieving the allelic locations of said first and said second heterologous DNA sequences providing for trans-splicing.

To the best of our knowledge, there is no prior art describing the use of ribozyme-mediated trans-splicing for assembly of useful traits in plant cells in a biologically safe and controllable way. The general scheme of trans-splicing mediated trait assembly in $F_1$ progeny is shown in FIG. 2A. None of two parental lines ($P_1$ and $P_2$) has a fully functional linear gene encoding said trait. In contrast, each contains fragments (A or B) of said gene preferably located on allelic chromosomes. As a result of pollination between $P_1$ and $P_2$, a progeny with a functional trait is generated by trans-splicing mediated assembly of fragments A and B. It is evident from said Figure, that only one fourth of $S_1$ progeny derived from self-pollination of the primary hybrid will retain the trait of interest, while the other half will inherit only one out of the two fragments required for providing said trait, and one fourth will have neither A or B. It is also evident, that cross-pollination with any other plant (illicit cross) having none of the fragments A and B will not lead to transmission of the trait, as only one of the two fragments necessary for functional gene is transmitted to each progeny plant.

Figure 3:
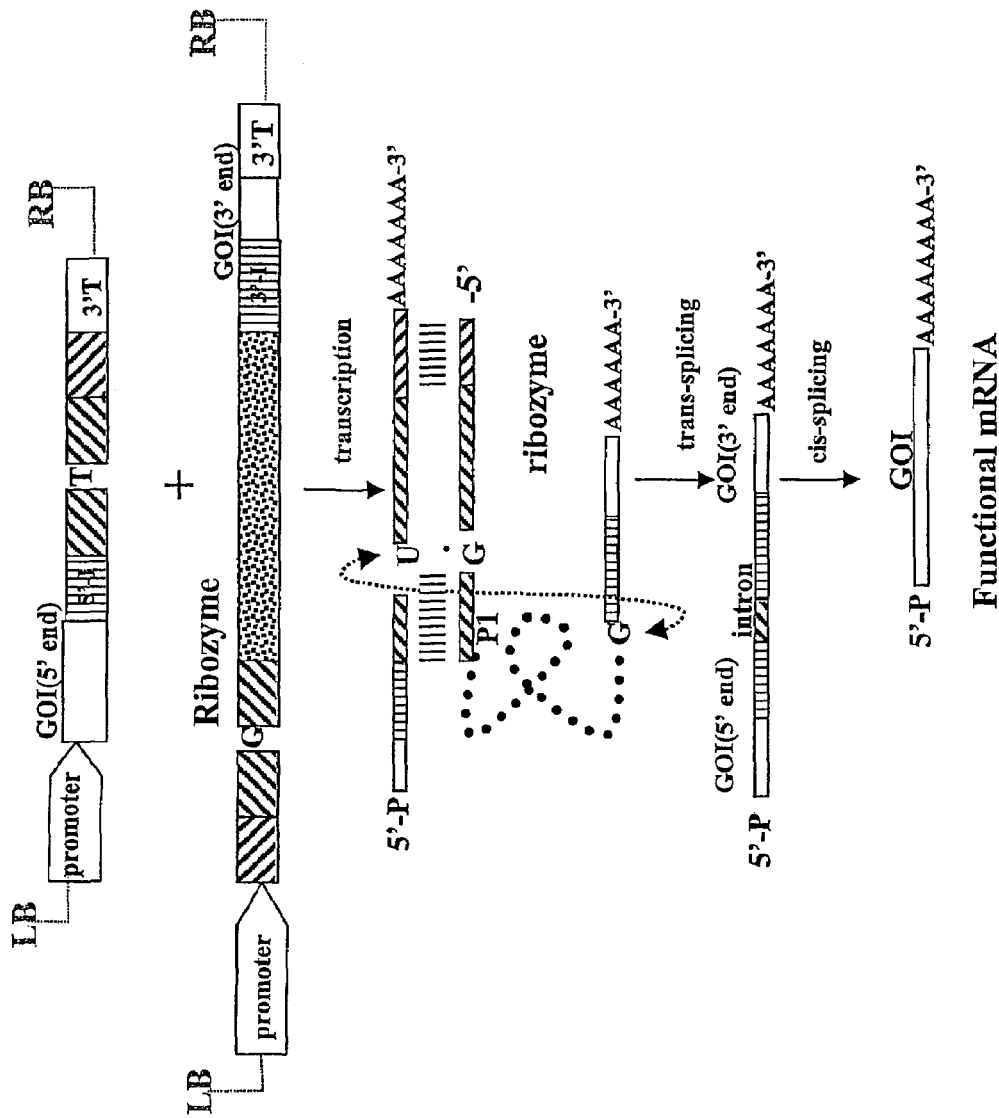
FIG. 3
Scheme of a process, where trans-splicing followed by cis-splicing leads to the assembly of a functional gene of interest (GOI) in plant cell.

Engineering ribozymes that are able to target selected RNA is not an ordinary task, as specific requirements to the ribozyme structure must be fulfilled. This might compromise the sequence of trans-spliced product and affect the choice of splicing site. To make this approach more flexible, an intron that hosts the trans-splicing site may be engineered. In this embodiment, trans-splicing will lead to the formation of a functional intron. Said intron can further undergo cis-splicing and yield functional RNA of a gene of interest (GOI) responsible for said trait of interest. The general scheme of this approach is shown in FIG. 3. Such approach, subject to testing for each specific ribozyme, is very useful for directed evolution/domain swap experiments, as it allows to engineer universal trans-splicing sites.

The trans-splicing of the invention is not limited to the use of group I introns and their derivatives. There are different groups/classes of introns classified according to their internal organization and mechanism of splicing. Nuclear introns have in common that they have GT-AG dinucleotides at the 5' and 3' ends and usually require spliceosome formation for their splicing. Group I and group II introns were named after introns found in different fungal mitochondrial genes. They are classified according to their internal organization but have in common the ability to autocatalyze their own splicing.

Nuclear introns are spliced by a snRNP-mediated (spliceosome-mediated) mechanism. There is abundant literature describing the mechanisms and design of cis-splicing including alternative splicing of nuclear genes in different eukaryotic organisms (for review see Adams et al., 1996, *Curr. Opin. Cell Biol.*, 8 331-339; Hastings & Krainer, 2001, *Curr. Opin. Cell Biol.*, 13, 302-309). Naturally occurring trans-splicing with the involvement of a snRNP-mediated mechanism is described for an attachement SL (spliced leader) RNA to the 5' end of mRNAs in trypanosomes (Agabian, N., 1990, *Cell*, 61, 1157-1160; Luo et al., 1999, *J. Biol. Chem.*, 274, 31947-31954) and *Caenorhabditis elegans* (Hirsh & Huang, 1990, *Mol. Biol. Rep.*, 14, 115). These small "spliced leader" RNAs consist of the 5' exon fused to sequences that can functionally substitute for U1 snRNA in mammalian snRNP-splicing extracts. Similar trans-splicing of SL RNA was also shown in chordates. In the ascidian protochordate *Ciona intestinalis* the mRNAs of at least seven genes undergo trans-splicing with SLRNAs (Vandenberghe et al., 2001, *Genes Dev.*, 15: 294-303). Trans-splicing of mRNAs was also demonstrated for mammalian cells (Eul et al., 1995, *EMBO J.*, 14, 3226-3235; Li et al., 1999, *J. Biol. Chem.*, 274, 11060-11071; Caudevilla et al., 2001, FEBS Lett., 507, 269-279) and *Drosophila* (Dorn et al., 2001, *Proc. Natl. Acad. Sci. USA*, 98, 9724-9729). An early indication that trans-splicing may function in plant nuclear RNA maturation came from analysis of the mRNA encoding a calcium-dependent seed-specific protein kinase (SPK) from-rice (Kawasaki et al., 1999, *Plant J.*, 18, 625-632). Mapping of a cDNA clone for SPK indicated that the entire cDNA was divided into two different regions, SPK-A and SPK-B, located on different rice chromosomes. There are reports by different groups, which clearly demonstrate that trans-splicing can be engineered by using splicesome-mediated mechanism (Puttaraju et al., 1999, *Nature Biotech.*, 17, 246-252; Liu et al., 2001, *Nature Biotech.*, 20, 47-52).

Group I and II introns have the ability to splice themselves out of pre-mRNA. This reaction can be performed in vitro by the RNA alone. Such RNAs with catalytic activities are generally called ribozymes. In this invention, the term ribozyme is used to name catalytic RNAs capable of performing trans-splicing reactions between separate RNA molecules. Both group I and group II introns are capable of trans-splicing in artificial systems (Been et al., 1986, *Cell*, 47, 207-216; Jacquier et al., 1986, *Science*, 234, 1099-1194; Jarrell et at., 1988, *Mol. Cell Biol.* 8, 2361-2366). Trans-splicing was also found for group II introns in split genes of chloroplasts (Kohchi et at., 1988, *Nucl. Acids Res.*, 16, 10025-10036), and for a group I intron in an artificially split gene in *Escherichia coli* (Galloway-Salvo et at., 1990, *J. Mol. Biol.*, 211, 537-549). Group I introns were first discovered in *Tetrahymena thermophila* rRNA (Cech, T. R., 1990, *Annu. Rev. Biochem.*, 59, 543-568). They require a U in the target sequence immediately 5' of the cleavage site and bind 4 to 6 nucleotides on the 5' side of the cleavage site. There are over 75 known members of this group up to now. They were also found in fungal and plant mitochondria (Richard & Dujon, 1997, *Curr. Genet.*, 32, 175-181; Cho et at, 1998, *Proc. Natl. Acad. Sci. USA*, 95, 14244-14249), chloroplasts (Turmel et at. 1993, *J. Mol. Biol.* 232, 446-46), phage T4 (Galloway et at, 1990, J. Mol. Biol., 211, 537-549), blue-green algae, and other organisms.

There are several developed approaches and engineered ribozymes which can be used to practice this invention (references cited above). They actually cover the use of all known types of introns in order to engineer trans-splicing events in eukaryotic cell. In addition to be used in this invention, ribozymes engineered on the basis of group I Tetrahymena introns (U.S. Pat. No. 6,015,794; Ayre et at., 1998, *Proc. Natl. Acad. Sci. USA*, 96, 3507-3512), spliceosome-mediated (Puttaraju et al., 1999, *Nature Biotech.*, 17, 246-252; Liu et al., 2001, *Nature Biotech.*, 20, 47-52; U.S. Pat. No. 6,083,702) or group II intron-mediated trans-splicing (Mikheeva & Jarrell, 1996, *Proc. Natl. Acad. Sci. USA*, 93, 7486-7490; U.S. Pat. No. 5,498,531) is also applicable.

Figure 4:
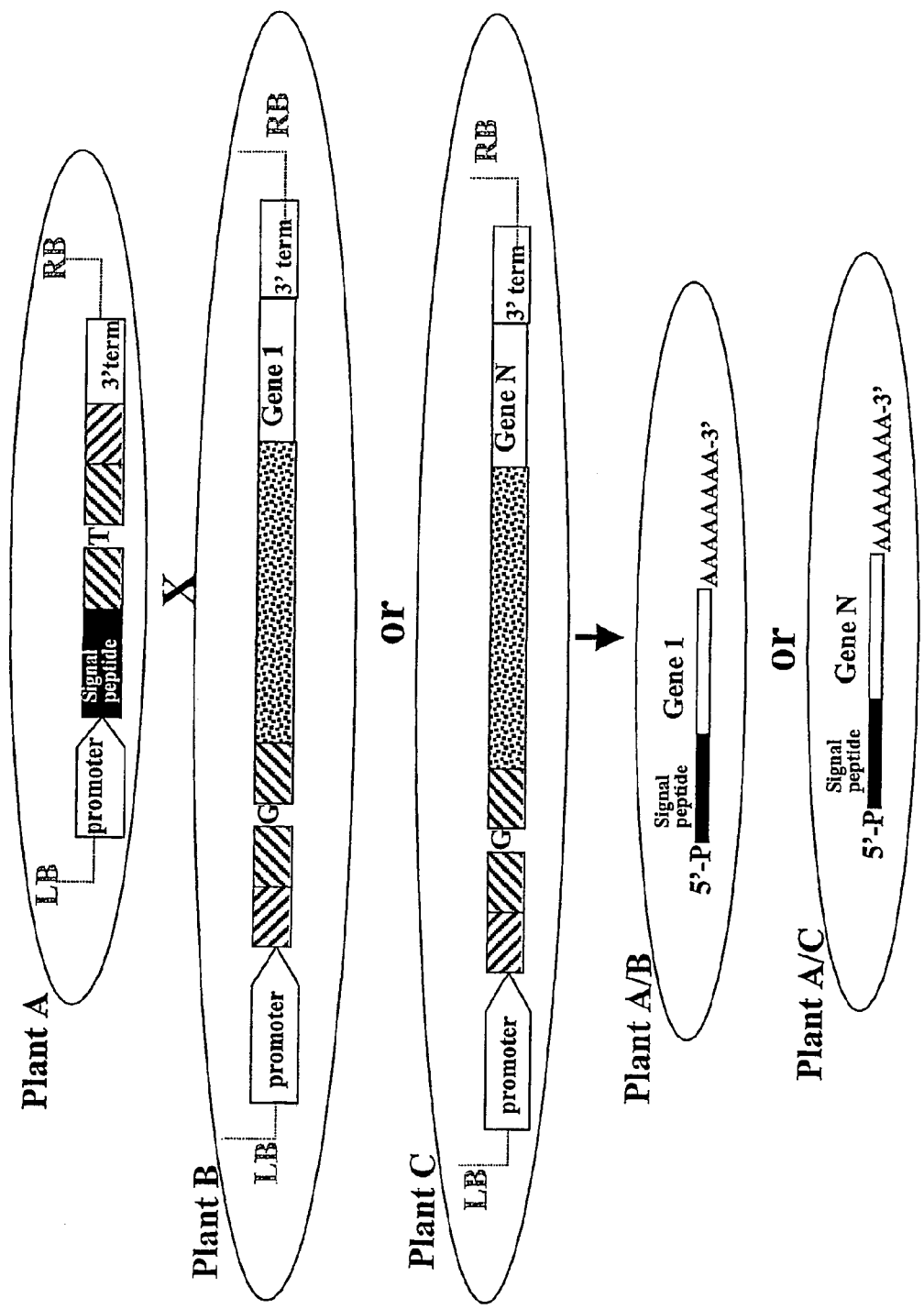
FIG. 4
General scheme of modular principle, where trans-splicing fuses a signal peptide of choice with different genes of choice, allowing compartmentalizing different gene products in hybrid progeny.

The processes of the invention may be used as a convenient way of assembling a desired sequence and/or expression unit from different parts in trans, using as modules or building blocks different transgenic plants (see FIG. 4). Their hybrid progeny would put together modules inherited from different parents through engineered ribozyme-mediated trans-splicing. It is possible to form a trait of interest by choosing the appropriate pair of transgenic parents containing required modules, very much like by choosing an appropriate pair of parental plants for producing high value hybrid seeds in traditional breeding. The examples of such modules include different signal peptides, binding domains, retention signals, compartmentalization signals, activation domains, domains with enzymatic activities, affinity tags, regulatory sequences, different genes of interest and parts thereof.

One application example of trans-splicing contemplated in our invention is the formation of herbicide-resistance and insect resistance by trans-splicing from non-functional precursors. In EXAMPLES 1 and 2 we describe the design of a system for ribozyme-mediated formation of BAR and CryIIIA mRNAs in plants. In the first example, we describe the design of two constructs containing said first and said second fragment of the invention of trans-splicing system for each gene of interest in trans. The formation of traits conferring PPT (herbicide phosphinothricin) and insect resistance occurs exclusively in plant cells harboring the two T-DNAs shown in FIG. 5.

Co-transformation of two T-DNAs can be easily selected using PPT containing media. The T-DNA linkage analysis is described in EXAMPLE 2, allowing to select the most appropriate transformant containing different T-DNAs on different allelic chromosomes, e.g. linked in repulsion.

Different strategies may be employed for introducing heterologous DNA sequences of interest in cells, notably in plant cells. One approach is based on generating two independent transformants, each of them containing one of the two heterologous DNA sequences involved in trans-splicing. These sequences can be brought together by sexual crossing or somatic cell hybridization through protoplasts fusion (Melchers, G.,1976, *Basic Life Sci.*, 8: 455-467; Ratushnyak et al., 1993, *Mol. Gen. Genet.*, 236: 427-432), thus providing for a trait of interest in their progeny. Alternatively, two heterologous DNA sequences can be stably integrated into the same plant cell during single or two independent transformation events. In both cases, genetic analysis of the progenies of such plants is preferably done in order to determine the linkage between said DNA fragments and to choose the most preferable location of said fragments relatively to each other. If said heterologous DNA sequences containing said fragments are introduced in different plants, they are not physically linked in a hybrid plant, but are located on different or allelic (linked in repulsion) chromosomes. In addition, there is a relatively high chance of said fragments being physically linked (located on the same chromosome) in case of stable integration of said fragments in the same plant.

Figure 2B:
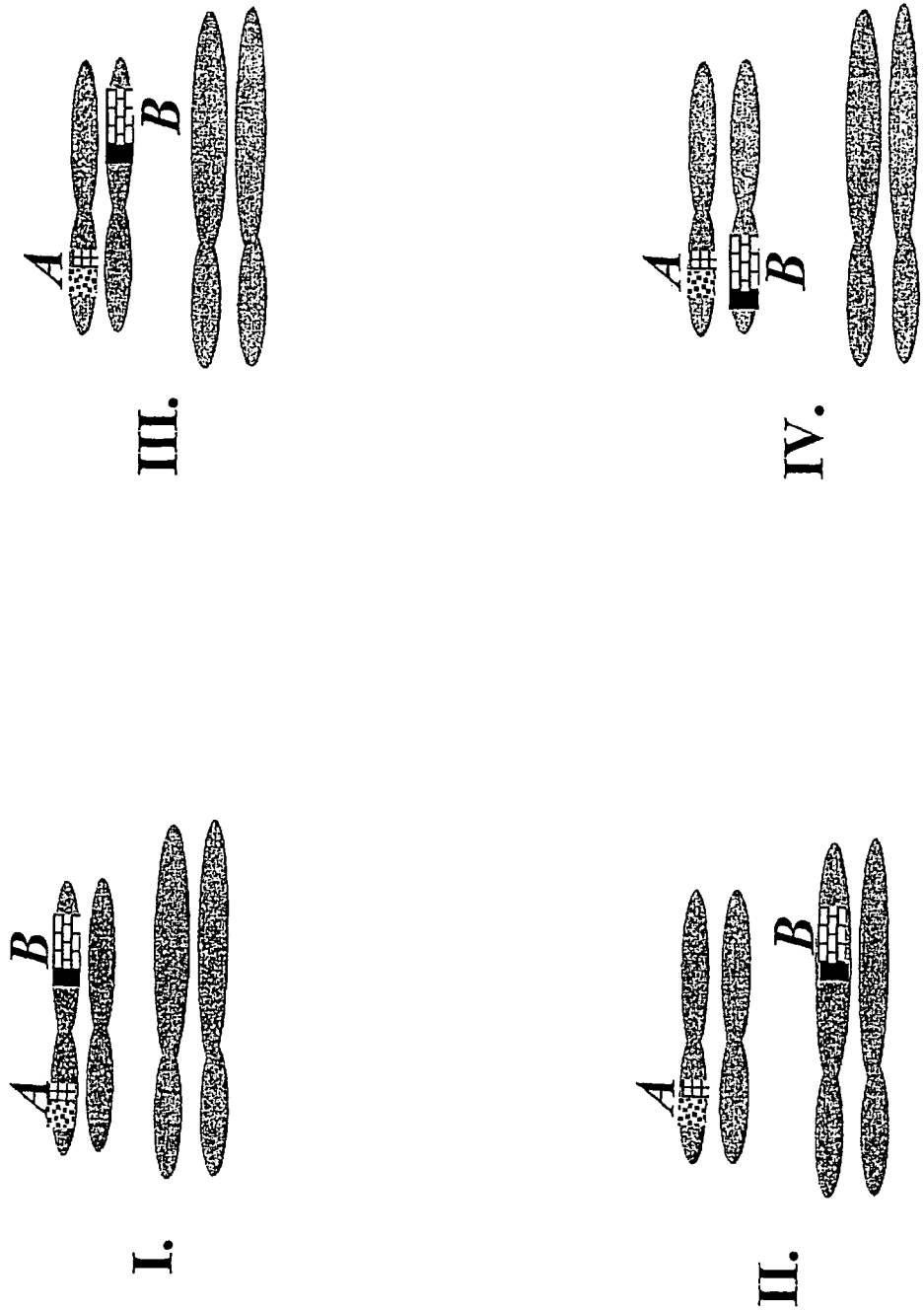

In one case, said two fragments are physically linked, e.g. are located on the same chromosome(FIG. 2B, case I). In this case, the fragments may segregate in progeny due to meiotic crossing over, thus giving better control over trait expression and movement than in the prior art, where said trait is encoded by one continuous sequence.

In a preferred embodiment, said fragments are not physically linked, e.g. are located on two different (non-homologous) chromosomes (FIG. 2B, case II). In this case, only half of self-progeny and one quarter of cross-progeny of the plant heterozygous for both fragments will inherit the trait.

More preferable, said fragments are on different allelic chromosomes (FIG. 2B, case III). Here, all self-progeny will inherit the trait, but no trait will be inherited by progeny resulting from crossing with plants possessing neither of said fragments if meiotic crossing-over is neglected or absent. Meiotic recombination between the two allelic chromosomes may, however, physically link said fragments A and B. The frequency of such recombination events directly depends from the relative distance between said fragments on two allelic chromosomes.

Figure 2C:
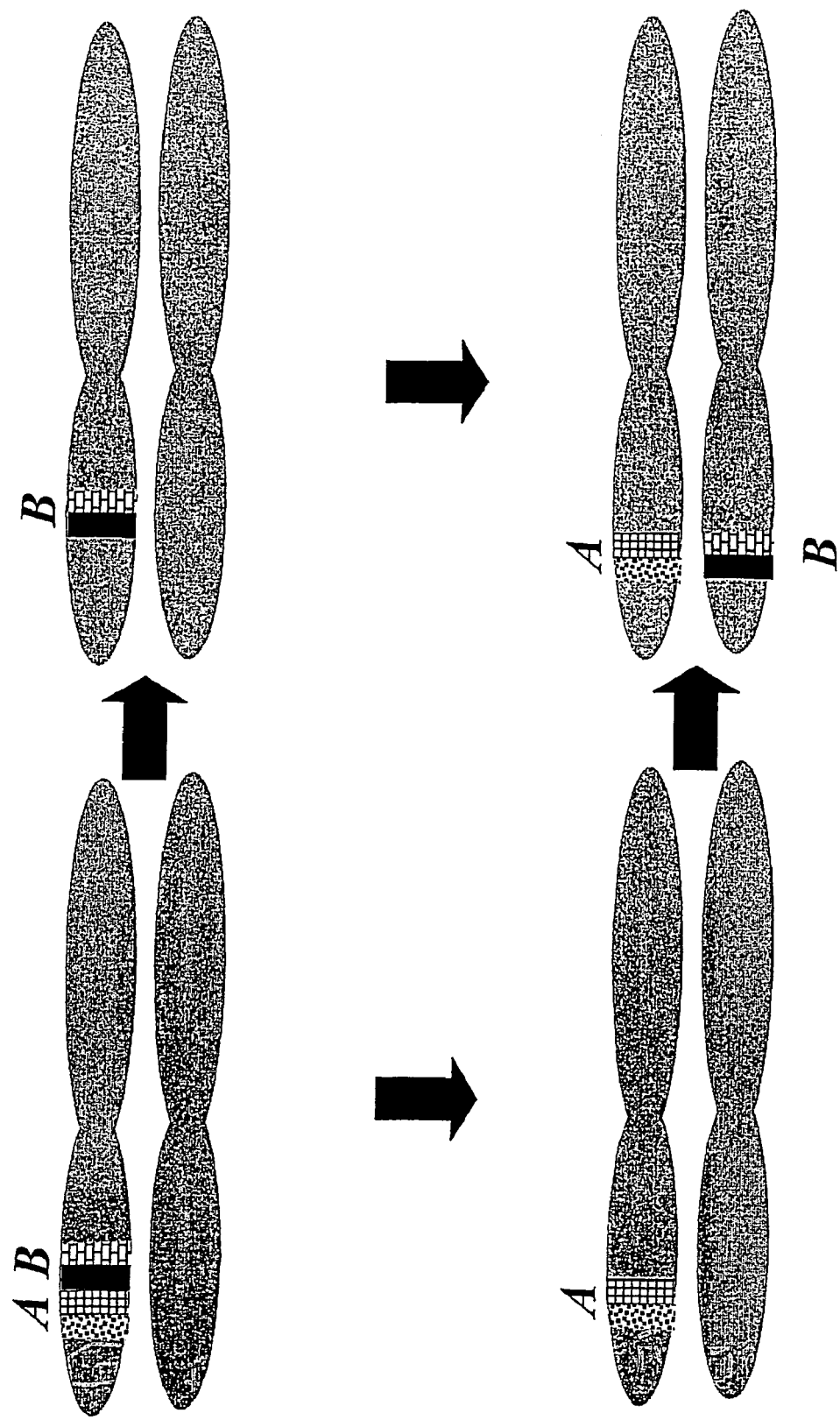

In order to suppress physical linkage of said fragments by meiotic recombination, said fragments are preferably positioned at short relative distance or, most preferably, at the same locus on different allelic chromosomes (FIG. 2B, case IV), thus minimizing the frequency of meiotic recombination between such fragments practically to zero. There are different technical solutions to achieve the most preferable allelic location of said fragments. Said fragments A and B can be integrated within chromosomal DNA as one construct AB (FIG. 2C). The design of the construct shall allow selectable removal of one of heterologous DNA fragments (A or B) using mechanism of controllable DNA rearrangement (excision, inversion or transposition), thus generating progeny containing either fragment A or fragment B in the same locus, or having selectively transcribed either fragment A or fragment B without removing them. Bringing together both fragments or their transcripts by crossing plants possessing only one of said fragments or both fragments, but only one of required transcripts, will lead to expressing a trait of interest. An example of controlled DNA recombination can be flanking fragments A and B with sequences recognized by different site-specific recombinases, and upon such recognition selectively removing either fragment A or fragment B. Alternatively, both fragments can be flanked by sequences for site specific recombination in such orientation, that exposure to the source of recombinase recognizing said sequences will lead to inversion of DNA fragment with both fragments. The placement of transcription initiation region (promoter) just outside of said DNA fragment can lead to transcription of fragment A or B depending on fragments orientation. Another approach comprises the use of transposition, where, for example fragment B is located and transcribed within a non-autonomous transposable element, but its excision from the construct will trigger transcription of fragment A. Excision of the transposon does not necessarily lead to its reinsertion elsewhere, so progeny can be selected that contains fragment A only.

In the examples, we used *Agrobacterium*-mediated T-DNA delivery in plant cells, whereby said T-DNA contains said first and/or said second heteologous sequence as a vector. Different methods may be used for the delivery of vectors into plant cells such as direct introduction of said vector into the cells by the means of microprojectile bombardment, electroporation or PEG-mediated transformation of protoplasts. *Agrobacterium*-mediated plant transformation is preferred, notably for process (i) and for said first heterologous sequence of process (ii). Thus, DNA may be transformed into plant cells by various suitable technologies such as by a Ti-plasmid vector carried by *Agrobacterium* (U.S. Pat. Nos. 5,591,616; 4,940, 838; 5,464,763), particle or microprojectile bombardment (U.S. Pat. No. 5,100,792; EP 00444882B1; EP 00434616B1). In principle, other plant transformation methods can also be used e.g. microinjection (WO 09209696; WO 09400583A1; EP 175966B1), electroporation (EP00564595B1; EP00290395B1; WO 08706614A1), etc. The choice of the transformation method depends on the plant species to be transformed. For example, microprojectile bombardment may be preferred for monocots transformation, while for dicots, *Agrobacterium*-mediated transformation gives generally better results.

The trans-splicing system described in our invention consists of two or more fragments which are provided in trans. This means that our system is better controlled and safer, e.g. it can have zero expression level in the uninduced state.

Genes of interest, or fragments thereof, that can be expressed, in sense or antisense orientation, using this invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active. toxin from *Bacillus thuringiensis* (Bt2 toxin, insecticidal crystal protein (ICP), CrylC toxin, delta endotoxin, polyopeptide toxin, protoxin etc.), insect specific toxin AaIT, cellulose degrading enzymes, E1 cellulase from *Acidothermus celluloticus,* lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed using the trans-splicing system. Examples of such proteins of interest include inter alia immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The process of the invention may further comprise expressing a gene encoding a post-transcriptional gene silencing (PTGS) suppressor protein or a function-conservative variant or fragment thereof into a plant for suppressing PTGS of said transgenic coding sequence. Said PTGS suppressor protein gene or function-conservative variant or fragment thereof may be provided to a plant on the same vector carrying said transgenic coding sequence or on an extra vector. Said PTGS suppressor protein is preferably of viral or plant origin. Examples of PTGS suppressor proteins are potato virus X p25 protein, african cassava mosaic virus AC2 protein, rice yellow mottle virus P1 protein, tomato bushy stunt virus 19K protein, rgs CAM or a function-conservative variant or fragment of one of these proteins. Said function-conservative variant or fragment preferably has a sequence identity of 75% to one of the above protein. Details on PTGS suppressor proteins and their use can be found in WO0138512.

Our invention is also applicable for selectable/scorable marker genes and their fusions with different genes of interest, thus allowing for the direct selection of the best recombinant protein producer. Examples of such selectable/scorable markers include inter alia genes or fragments of: neomycin phosphotransferase II (NPTII), hygromycin phosphotransferase, aminoglycoside 6'-N-acetyltransferase, 5-enolpyruvylshikimate-3-phosphate synthase, phosphinothricin acetyl transferase (BAR), betaine aldehyde dehydrogenase (BADH), dihydrofolate reductase (DFR1), 6' gentamicin acetyltransferase (6' GAT), acetolactate synthase (ALS), phosphomannose-isomerase (PMI), glyphosate oxidoreductase, acetohydroxyacid synthase (AHAS), 2-deoxyglucose-6-phosphate phosphatase (2-DOG-6-P), luciferase, green fluorescent protein (GFP), and selectable and screenable marker genes fusions.

EXAMPLE 1

Figure 5:
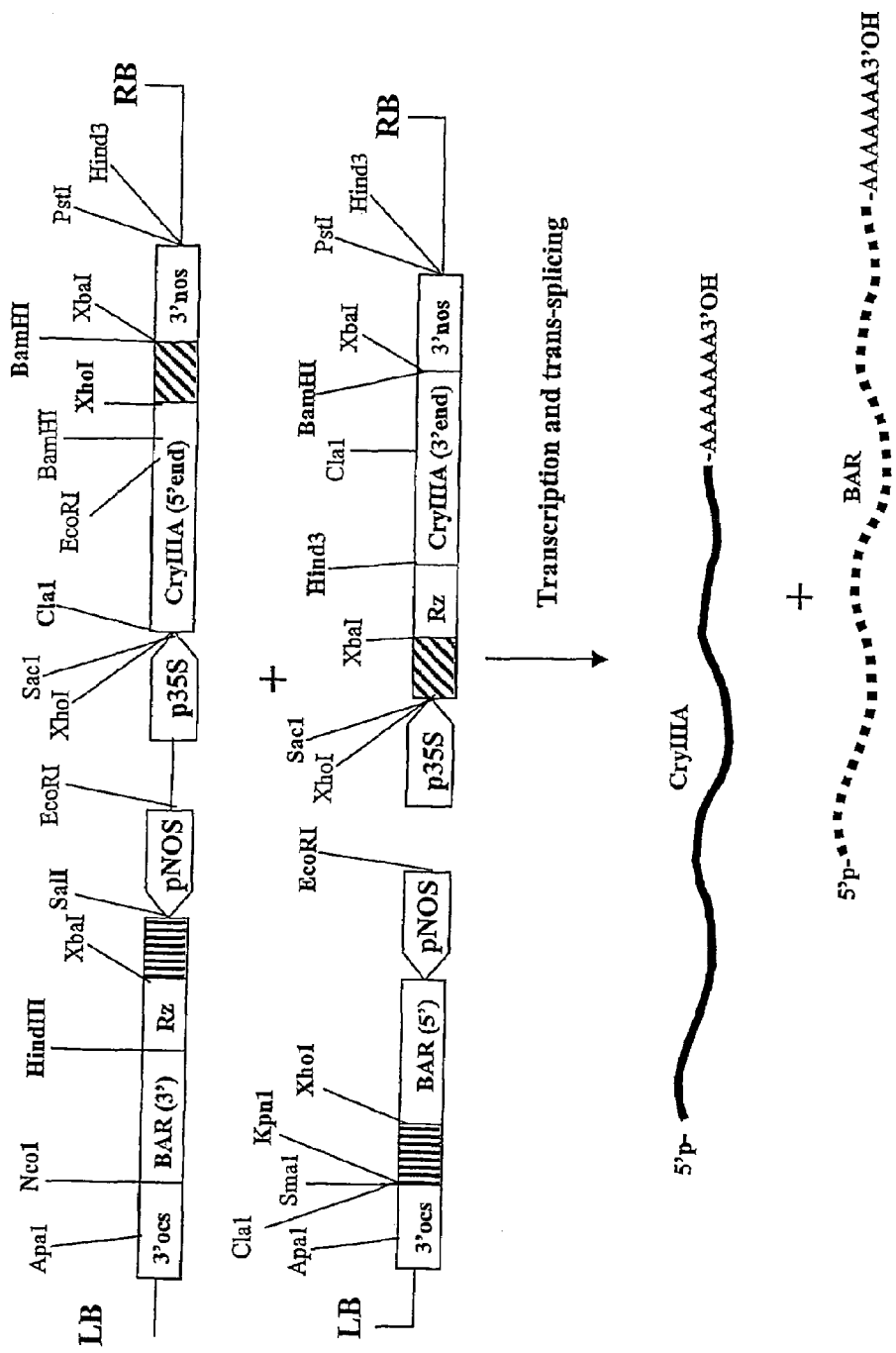
FIG. 5
Scheme of a process, where trans-splicing leads to the formation of transcripts providing for insect- and herbicide-resistance traits. Rz stands for ribozyme.
Figure 6:
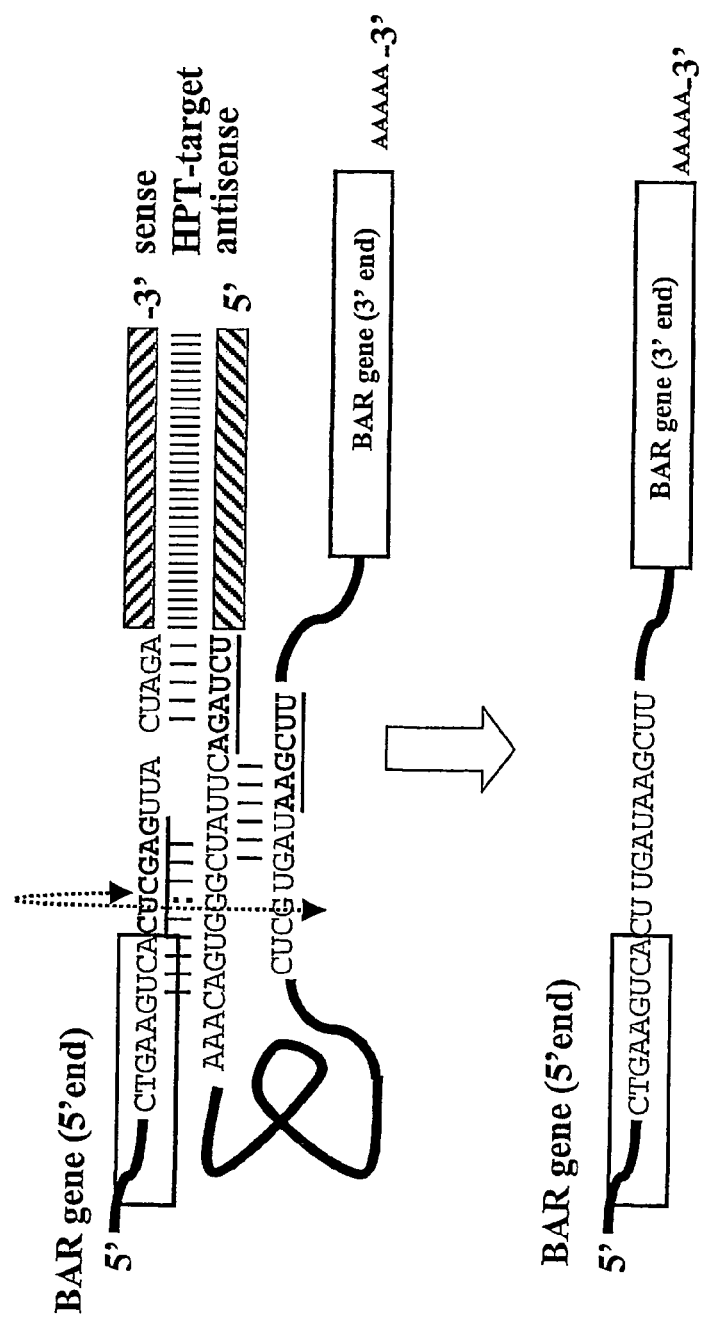
FIG. 6
Detailed scheme of complementary RNA interaction for ribozyme-mediated trans-splicing of BAR gene fragments.

Construct Design for Trans-Splicing-Mediated BAR and CryIIIA Transcript Assembly Two T-DNA constructs (see FIG. 5), one with ribozyme linked to 3' end of BAR gene (Gene Bank Accession X17220) and 5' end of CryIIIA gene (Gene Bank Accession X70979) and another—with 5' end of BAR gene and ribozyme linked with 3' end of CryIIIA gene, were designed using standard molecular biology techniques (Sambrook, Fritsch & Maniatis, 1989, *Molecular Cloning: A Laboratory Manual*, Cold Spring Harbor Lab Press, Plainview, N.Y., 2nd edition). The first construct (FIG. 5, top) carries the 5' end of a 35S promoter-driven transcriptional unit containing a CryIIIA gene linked to a 200 b.p. fragment of HPT gene in sense orientation and a nos promoter-driven transcriptional unit containing 300 b.p. HPT gene fragment in anti-sense orientation followed by a ribozyme linked to 3'end of BAR gene. The second construct (FIG. 5, second from the top) has a 35S promoter-driven 200 b.p HPT gene fragment in anti-sense orientation followed by a ribozyme linked to the 3'end of the CryIIIA gene and a nos promoter-driven 5' end of the BAR gene linked with a 300 b.p. HPT fragment in sense orientation. Schematic presentations of the constructs as well as the products of trans-splicing are shown in FIG. 5. FIG. 6 shows a detailed picture of the trans-splicing process yielding a functional BAR gene.

Cloning of the 5' End of Trans-Splicing System—BAR Gene.

A part of the HPT gene (300 nucleotides, Gene Bank Accession No. V014999, the sequence is shown below) was chosen as the target sequence. HPT is a bacterial gene, it is not related to any of the plant genes. The G/C content is about 60%, so base pairing between 5' and 3' parts of the viral vector should be quite efficient:

```
Pnos1:
5'-ctagaattcatgagcggagaattaagggagtc-3'
      EcoRI

Bar1r:
5'-gtaactcgagtgacttcagcaggtgggtgtag-3'
       XhoI
```

The 5' end of BAR gene together with nos promoter was PCR amplified using plCBV19 plasmid DNA (FIG. 7) as template and primers pnos1 and bar1r. This PCR fragment was digested with Xho1 and EcoRI and cloned into the large fragment of Kpn1-EcoRI digested binary plCBV19 together with targhpt1-targhpt5 amplified and digested with Kpn1 and Xho1 restriction enzymes HPT fragment. This yielded plCBV19 containing 5' end of the BAR gene linked to 300 bp of HPT coding sequence under control of NOS promoter (intermediate construct1).

Construct plCH1600, containing HPT gene, was taken as template for PCR amplification of the HPT fragments.

Cloning of the 3'-End of the Trans-splicing System—BAR Gene.

```
attgctgatccccatgtgtatcactggcaaactgtgatggacgacaccgtcagtgcgtccgtcgcgcaggctctcgatgagctgat gctttgggccgaggactgccccgaagtccggcacctcgtgcacgcggatttcggctccaacaatgtcctgacggacaatggcc gcataacagcggtcattgactggagcgaggcgatgttcggggattcccaatacgaggtcgccaacatcctcttctggaggccgt ggttggcttgtatggagcagcagacgcgctacttcgagcggaggcat
```

The following primers were used for the amplification of the 300 bp HPT-target sequence: (restriction sites are written in bold letters and underlined):

```
Targhpt1:
5'-atgcctcgagttactagaattgctgatccccatgtgtatcac-3'
       XhoI

Targhpt3:
5'-tcaggtcgacatgcctccgctcgaagtagcgcgt-3'
       SalI

Targhpt4:
5'-tgactctagaattgctgatccccatgtgtatcac-3'
       XbaI

Targhpt5:
5'-tcagggtaccatgcctccgctcgaagtagcgcgt-3'
       Kpn1
```

The coding sequence of BAR gene was split in two parts at the middle of acetyltransferase domain (AA residues 60-142) to ensure there is no phosphinothricin resistance provided by any of separate parts. The primers used to PCR the fragments of interest are:

For cloning 3' end of BAR gene linked with ribozyme, the Kpn 1-EcoR 1 fragment of plCBV19 (pNOS-BAR) was replaced with pNOS promoter separated from 3' OCS transcription termination signal by Sal1 and Nco 1 restriction sites.

The following primers were used to amplify the 3'end of the BAR gene:

```
Bar2f:
5'-ggagaagcttggcttcaagagcgtggtcgctg-3';
       HindIII

Bar3r:
5'-catgccatggtcaaatctcggtgacgggcaggacc-3'.
       Nco1
```

Sequence of synthetic ribozyme based on group I intron was taken from *Tetrahymena thermophila* precursor 26S rRNA (Koehler et al., 1999, J. Mol. Biol., 285, 1935-1950; Ayre et al., 1999, Proc. Natl. Acad. Sci. USA, 96, 3507-3512).

```
XbaI
tctagacttatcgggtgacaaaagttatcaggcatgcacctggtagctagtcttttaaaccaatagattgcatcggtttaaaaggca agaccgtcaaattgcgggaaaggggtcaacagccgttcagtaccaagtctcaggggaaactttgagatggccttgcaaagggt atggtaataagctgacggacatggtcctaaccacgcagccaagtcctaagtcaacagatcttctgttgatatggatgcagttcaca
```

-continued

```
gactaaatgtcggtcggggaagatgtattcttctcataagatatagtcggacctctccttaatgggagctagcggatgaagtgatgc aacactggagccgctgggaactaatttgtatgcgaaagtatattgattagttttggagtactcgtgataagctt
                                                                   HindIII
```

This ribozyme sequence was ordered at ATG:Biosynthetics GmbH (P0202001), inserted into pBluescript II SK(+) between HindIII and XbaI restriction sites (plasmid pICH080) and used for further cloning steps. Then ribozyme from pIC080 (HindIII/XbaI) was fused to the antisense version of the HPT-target (300 bp XbaI/SaI1 PCR fragment amplified with primers Targhpt3 and Targhpt4) to get the intermediate plasmid based on pBS(KS+). This plasmid was used to isolate Hind III/SaI 1 fragment of ribozyme linked with 300 b.p of HPT fragment in antisense orientation.

Figure 7:
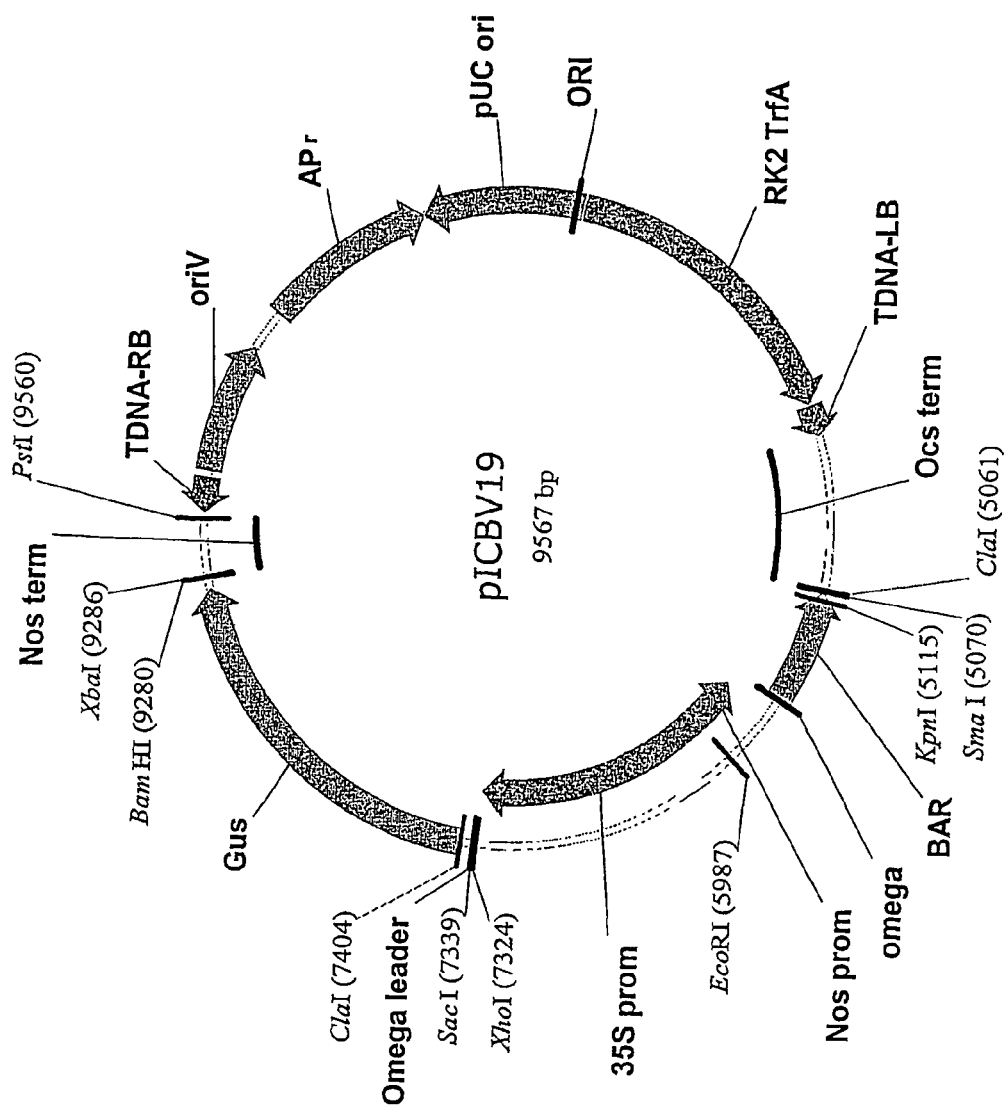
FIG. 7 depicts binary vector plCBV19.

The final step in cloning of this expression cassette included three-way ligation of HindIII/SaII ribozyme-HPT fragment with HindIII/NcoI-treated PCR fragment (primers bar2f and bar3r) of 3' end of the BAR gene and NcoI/SaI1 digested modified binary vector pICBV19 (FIG. 7). The final cloning yielded pICBV19 containing ribozyme linked to the 3' end of the BAR gene under control of NOS promoter (intermediate construct 2).

The process of cloning BAR gene into two fragments and their assembly through trans-splicing led to the neutral substitution of three non-conserved amino acid residues in the region of split (Glu-Asp; Ala-Lys; Gln-Leu).

Cloning of the 5'-End of the Trans-splicing System—CryIIIA Gene

A part of the HPT gene (180 nucleotides, Gene Bank Accession No. V014999, the sequence is shown below) was chosen as the target sequence in this case.

```
5'-ctgaactcac cgcgacgtct gtcgagaagt ttctgatcga
aaagttcgac agcgtctccg acctgatgca gctctcggag ggcgaagaat ctcgtgcttt cagcttcgat gtaggagggc
gtggatatgt cctgcgggta aatagctgcg ccgatggttt ctacaaagat cgttatgttt-3'
```

This sequence does not overlap with the 300 b.p. HPT fragment used for designing ribozyme-mediated trans-splicing system for the BAR gene.

For cloning with 5' end of CryIIIA gene, the 180 b.p. HPT fragment was amplified with hpt1f (5'-gcatctcgag ttactagact gaactcaccg cgacgtct gtc-3', SEQ ID NO: 12) and hpt2r (5'-ctgcggatc caaacataac gatcttgtag aaaccatcc-3', SEQ ID NO: 13) primers, digested with Xho1 and BamH1 and ligated together with Cla1/Xho1 synthetic fragment of CryIIIA gene (ATG:Biosynthetics GmbH) into gel-purified large Cla1/BamH1 fragment of intermediate construct 2. The restriction sites for Xho1 and BamH1 in primer sequences are shown in bold. The final construct is shown in FIG. 5 (top).

The 5' fragment of synthetic CryIIIA gene with 5' end of rice actin 1 intron (shown in italic, Gene Bank Acc. No X63830) flanked by Cla1 (5' end) and Xho1 (3' end) restriction sites (SEQ ID NO: 14):

```
  Cla1
5'-atcg atgactgcag acaacaacac cgaagccctc
gacagttcta ccactaagga tgttatccag aagggtatct ccgttgtggg agacctcttg ggcgtggttg gatttccctt
cggtggagcc ctcgtgagct tctatacaaa ctttctcaac
```

```
accatttggc caagcgagga cccttggaaa gcattcatgg
agcaagttga agctcttatg gatcagaaga ttgcagatta tgccaagaac aaggctttgg cagaactcca gggccttcag
aacaatgtgg aggactacgt gagtgcattg tccagctggc agaagaaccc tgttagctcc agaaatcctc acagccaagg
taggatcaga gagttgttct ctcaagccga atcccacttc agaaattcca tgcctagctt tgctatctcc ggttacgagg
ttcttttcct cactacctat gctcaagctg ccaacaccca cttgtttctc cttaaggacg ctcaaatcta tggagaagag
tggggatacg agaaagagga cattgctgag ttctacaagc gtcaacttaa gctcacccaa gagtacactg accattgcgt
gaaatggtat aacgttggtc tcgataagct cagaggctct tcctacgagt cttgggtgaa cttcaacaga tacaggagag
agatgacctt gactgtgctc gatcttatcg cactctttcc cttgtacgat gtgagactct acccaaagga agtgaaaact
gagcttacca gagacgtgct cactgaccct attgtcggag tcaacaacct taggggttat ggaactacct
                                          EcoR1 tcagcaatat cgaaaactac attaggaaac cacatctctt
cgactatctt cacagaattc aattccacac aag gtaaccaccc cgcgtccctc tcctctttct ttctccgttt
tttttttccg tctcgtctcg atctttggcc ttggtagttt
gggggcgaga ggcggcttcg tcgcccagat cggtgcgcgg gaggggcggg
                                                      BamH1
atctcgcggc tgggtctcgg cgtgcggccgatcctcgcg
gggaatgggg ctctcggatg tagatctgat ccgccgttgt tgggggagat gatgggggcgt ttaaaatttc aagtcactcg ag-3'
                                                 XhoI
```

The 3' fragment of synthetic CryIIIA gene preceeded by 3' end of rice actin 1 intron (shown in italic) and flanked by HindIII (5' end) and BamH1 (3' end) restriction sites (SEQ ID NO: 15):

```
HindIII
5'aagctt gccatgctaa acaagatcag gaagagggga
aaagggcact atggtttata tttttatata tttctgctgc tgctcgtcag gcttagatgt gctagatctt tctttcttct
ttttgtgggt agaatttgaatccctcagca ttgttcatcg
gtagtttttc ttttcatgat ttgtgacaaa tgcagcctcg tgcggagctt
ttttgtag gtttcaa ccaggatact atggtaacga ctccttcaac tattggtccg gtaactatgt ttccaccaga ccaagcattg
gatctaatga catcatcaca tctcccttct atggtaacaa gtccagtgaa cctgtgcaga accttgagtt caacggcgag
aaagtctata gagccgtcgc aaacaccaat ctcgctgtgt ggccatccgc agtttactca ggcgtcacaa aggtggagtt
tagtcagtat aacgatcaga ccgatgaggc cagcacccag
```

-continued

```
acttacgact ccaaacgtaa cgttggcgca gtctcttggg
attctatcga ccaattgcct ccagaaacca cagacgaacc attggagaag ggctacagcc accaacttaa ctatgtgatg
tgcttcttga tgcaaggttc cagagggacc attccagtgt tgacctggac acacaagtcc gtggacttct tcaacatgat
cgatagcaag aagatcactc aacttccctt ggtgaaagcc tacaagctgc
aatctggtgc ttccgttgtc gcaggtccca gattcactgg aggtgacatc atccagtgca
cagagaacgg cagcgcagct actatctacg tgacacctga tgtgtcttac tctcagaagt
acagggcacg tattcattac gcatctacca gccagatcac cttcacactc agcttggatg
gagcaccctt caaccagtat tactttgaca agaccatcaa caaaggtgac actctcacat
acaatagctt caacttggca agtttcagca caccatttga actctcaggc aacaatcttc
agatcggcgt caccggtctc agcgccggag acaaagtcta catcgacaag attgagttca
tcccagtgaa ctgaggatcc
                                                BamHI
```

The region between two conserved blocks (block 2 and block 3) within domain II was chosen for the split of CryIIIA in two parts (Schnepf et al., 1998, *Microbiol & Mol. Biol. Rev.*, 62, 775-806).

Cloning of the 3'-end of the Trans-splicing System—CryIIIA Gene.

The Hind111/Xba1 fragment of ribozyme was cloned together with 180 b.p. Sac1/Xba1 HPT fragment into Sac1/Hind 111 sites pBS(KS+), creating ribozyme fragment linked with HPT gene fragment in anti-sense orientation. The HPT fragment was PCR-amplified with primers hpt3f (5'- gcatagatctct gaactcaccg cgacgtct gtc-3', SEQ ID NO: 16) and hpt4r (5'-ctgcgagctcaaacataac gatcttgtag aaaccatcc-3', SEQ ID NO: 17) using the plasmid pICH1600 as the template. The synthesized Hind111/BamH1 fragment containing 3' end of cryIIIA fragment preceded by 3'end of rice actin 1 gene intron (see above), was cloned together with Hind111/Sac1 fragment of Ribozyme-HPT into Sac1/BamH1 sites of intermediate construct 1, replacing GUS gene with ribozyme-linked 3' part of CryIIIA and generating final construct (see FIG. 5, second from the top).

EXAMPLE 2

Detection of Trans-splicing Events in Transformed Plant Cells

The T-DNA of constructs shown in FIG. 5, were co-introduced in *Arabidopsis thaliana* (Col-0) plants as descried by Bent et al., (1994, *Science*, 285, 1856-1860). Seeds were harvested three weeks after vacuum-infiltration germinated and screened for transformants, by spraying several times with 50 mg/L of phosphinothricin (PPT) solution.

The same constructs were also used for *Agrobacterium*-mediated leaf disc cotransformation of *Nicotiana* plants (Horsh et al., 1985, *Science*, 227, 1229-1231) using 10 mg/L of PPT.

The transgenic plants showing resistance to PPT, shall harbor two different T-DNAs, carrying the different parts of BAR gene. No PPT resistant plants were recovered by using only one of two constructs. This suggests that CryIIIA also shall be present in the cell, as its parts are linked with BAR gene fragments.

Southern analysis was performed to select transgenics with single copy of each T-DNA.

Genetic analysis of the $T_1$ (self of $T_0$) and F1 ($T_0$×w.t.) progenies of primary transformants ($T_0$) allows to select for transgenic plants carrying two functionally complementary T-DNAs on the same, different or allelic chromosomes. For example, $T_1$ showing segregation $PPT^T:PPT^S=3:1$ and $F_1$ segregating $PPT^T:PPT^S=1:1$, means the T-DNAs are linked and can segregate only as a result of meiotic cross-over. The case, where $T_1$ showing segregation $PPT^T:PPT^S=9:7$ and $F_1$ segregating $PPT^T:PPT^S=1:3$, means the T-DNAs are located on different non-allelic chromosomes. The $T_1$ showing segregation $PPT^T:PPT^S=1:1$ and $F_1$ segregating $PPT^T:PPT^S=0:1$, means the T-DNAs are located on allelic chromosomes. The latter case will preferable to work with, as the transfer of herbicide resistance and insect resistance traits through cross-polination will be very limited.

The invention claimed is:

1. A process of producing a transgenic multi-cellular plant organism expressing a trait of interest and having a controlled distribution of said trait to progeny, wherein said process comprises sexual crossing of
a first multi-cellular plant organism having a first heterologous DNA sequence comprising a first fragment of a nucleotide sequence conferring said trait of interest and a second multi-cellular plant organism having a second heterologous DNA sequence comprising a second fragment of the nucleotide sequence conferring said trait of interest, wherein at least one of said first and said second heterologous DNA sequences encodes a ribozyme for trans-splicing, and wherein the trans-splicing ribozyme is a *Tetrahymena thermophila* 26S rRNA, group I intron-derived ribozyme,
whereby said first and said second heterologous sequences are designed such that said trait of interest arises due to RNA trans-splicing after said sexual crossing, and
whereby said first and said second fragment of a nucleotide sequence conferring said trait of interest are present on allelic chromosomes, wherein said first and/or said second heterologous sequence contains an intron or a part thereof such that the RNA product of the trans-splicing reaction contains an intron capable of cis-splicing.

2. The process according to claim 1, wherein said controlled distribution means that, upon crossing of said transgenic multi-cellular organism with an organism devoid of said first and said second heterologous sequences, the frequency of the appearance of said trait in descendent organisms is less than 1%.

3. The process according to claim 1, wherein said transgenic multi-cellular plant is incapable of expressing said trait of interest in the absence of either said first or said second heterologous sequence.

4. The process according to claim 1, wherein said trans-splicing results in messenger RNA capable of translating and producing a protein, thus endowing said transgenic multi-cellular plant organism with said trait of interest.

5. The process according to claim 1, wherein said trans-splicing results in a plurality of expressible messenger RNAs, thus generating multiple proteins or different chimeric proteins.

6. The process according to claim 1, wherein said multi-cellular organism is provided with said first or said second heterologous sequence by viral transfection, *Agrobacterium*-mediated delivery, non-biological delivery, or by conversion of (a) polynucleotide molecule(s) that was pre-integrated into a nuclear DNA or was maintained in the nucleus autonomously, to form said first or said second heterologous sequence.

7. The process according to claim 6, comprising stable transformation and stable integration of said first and/or said second heterologous sequence into a chromosome of said multi-cellular organism.

8. The process according to claim 1, wherein said multi-cellular organism is further genetically or transiently modified for providing functions necessary for said trans-splicing and/or said expressing of the trait of interest.

9. The process according to claim 1, wherein said first and/or said second fragment is operably linked to more than one nucleic acid encoding more than one trans-splicing ribozyme or to two or more different trans-splicing ribozymes.

10. The process according to claim 1, wherein said trait of interest is involved in male sterility.

11. The process according to claim 1, wherein said trait is selected from the group consisting of herbicide resistance, insect resistance, a selectable marker, and a counter-selectable marker.

12. The process according to claim 1, wherein expression of said trait of interest depends on the correct processing of said first and/or said second heterologous sequence(s).

13. The process according to claim 1, wherein said first and said second heterologous sequences in said transgenic multi-cellular plant organism segregate as unlinked loci.

14. The process according to claim 13, wherein said unlinked loci are positioned so as to minimize recombination and creation of linkage between said loci.

15. The process according to claim 1, wherein said first and said second heterologous sequences in said transgenic multi-cellular plant organism are located in the same locus on said allelic chromosomes.

16. The process according to claim 1, wherein the trans-splicing reaction and translation of the product of said trans-splicing reaction generates a protein having a polypeptide linked thereto by said trans-splicing reaction, whereby said polypeptide is selected from the group consisting of signalling, targeting, and membrane transduction polypeptides, and recognition and purification tags.

17. The process according to claim 1, wherein said transgenic multi-cellular organism is capable of producing progeny.

18. The process according to claim 1, wherein said first multi-cellular organism is made homozygous with respect to said first heterologous DNA sequence and said second multi-cellular organism is made homozygous with respect to said second heterologous DNA sequence.

19. The process according to claim 1, wherein said process is used for producing hybrid seeds of said transgenic multi-cellular plant.

20. A transgenic multi-cellular plant organism expressing a trait of interest, said organism having a controlled distribution of said trait to progeny, wherein expression of said trait involves production of an RNA molecule by trans-splicing of RNA fragments, wherein said multi-cellular plant organism has a first heterologous DNA sequence and a second heterologous DNA sequence, said first heterologous DNA sequence comprising a first fragment of a nucleotide sequence conferring said trait of interest and said second heterologous DNA sequence comprising a second fragment of the nucleotide sequence conferring said trait of interest, wherein at least one of said first and said second heterologous DNA sequences encodes a ribozyme for trans-splicing, and wherein the trans-splicing ribozyme is a *Tetrahymena thermophila* 26S rRNA, group I intron-derived ribozyme, whereby said first and said second heterologous sequences are designed such that said trait of interest arises due to RNA trans-splicing, whereby said first and said second fragment of a nucleotide sequence conferring said trait of interest are present on allelic chromosomes, and wherein said first and/or said second heterologous sequence contains an intron or a part thereof such that the RNA molecule contains an intron capable of cis-splicing.

* * * * *

UNITED STATES PATENT AND TRADEMARK OFFICE
CERTIFICATE OF CORRECTION

PATENT NO. : 7,632,981 B2
APPLICATION NO. : 10/512879
DATED : December 15, 2009
INVENTOR(S) : Werner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,632,981 B2 | Page 1 of 4 |
| APPLICATION NO. | : 10/512879 | |
| DATED | : December 15, 2009 | |
| INVENTOR(S) | : Werner et al. | |

It is certified that error appears in the above-identified patent and that said Letters Patent is hereby corrected as shown below:

Column 15,
Lines 25-35,
"     attgctgatccccatgtgtatcactggcaaactgtgatggacgacaccgtcagtgcgtccgtcgcgcaggctctcgatgagctgatgcttt
gggccgaggactgccccgaagtccggcacctcgtgcacgcggatttcggctccaacaatgtcctgacggacaatggccgcataac
agcggtcattgactggagcgaggcgatgttcggggattcccaatacgaggtcgccaacatcctcttctggaggccgtggttggcttgtat
ggagcagcagacgcgctacttcgagcggaggcat                                                                                   "

should read

--    attgctgatccccatgtgtatcactggcaaactgtgatggacgacaccgtcagtgcgtccgtcgcgcaggctctcgatgagctgatgcttt
gggccgaggactgccccgaagtccggcacctcgtgcacgcggatttcggctccaacaatgtcctgacggacaatggccgcataac
agcggtcattgactggagcgaggcgatgttcggggattcccaatacgaggtcgccaacatcctcttctggaggccgtggttggcttgtat
ggagcagcagacgcgctacttcgagcggaggcat (SEQ ID NO: 1)                                                      --

Lines 40-42,
"   Targhpt1:
    5'-atgcctcgagttactagaattgctgatccccatgtgtatcac-3'
           XhoI                                                              "

should read

--   Targhpt1:
    5'-atgcctcgagttactagaattgctgatccccatgtgtatcac-3' (SEQ ID NO: 2)
           XhoI                                                              --

Lines 43-45,
   Targhpt3:
    5'-tcaggtcgacatgcctccgctcgaagtagcgcgt-3'
"        SalI                                                                   "

should read

Signed and Sealed this
Twenty-fifth Day of January, 2011

David J. Kappos
*Director of the United States Patent and Trademark Office*

Column 15 (continued),
Targhpt3:
5'-tcaggtcgacatgcctccgctcgaagtagcgcgt-3' (SEQ ID NO: 3)
-- SalI --

Lines 47-49,
Targhpt4:
5'-tgactctagaattgctgatccccatgtgtatcac-3'
" XbaI "

should read

Targhpt4:
5'-tgactctagaattgctgatccccatgtgtatcac-3' (SEQ ID NO: 4)
-- XbaI --

Lines 50-52,
Targhpt5:
5'-tcagggtaccatgcctccgctcgaagtagcgcgt-3'
" KpnI "

should read

Targhpt5:
5'-tcagggtaccatgcctccgctcgaagtagcgcgt-3' (SEQ ID NO: 5)
-- KpnI --

Column 16,
Lines 3-5,
Pnos1:
5'-ctagaattcatgagcggagaattaagggagtc-3'
" EcoRI "

should read

Pnos1:
5'-ctagaattcatgagcggagaattaagggagtc-3' (SEQ ID NO: 6)
-- EcoRI --

Lines 6-8,
Bar1r:
5'- gtaactcgagtgacttcagcaggtgggtgtag-3'
" XhoI "

should read

Bar1r:
5'- gtaactcgagtgacttcagcaggtgggtgtag-3' (SEQ ID NO: 7)
-- XhoI --

CERTIFICATE OF CORRECTION (continued)
U.S. Pat. No. 7,632,981 B2

Column 16 (continued),
Lines 46-48,
  Bar2f:
  5'-ggagaagcttggcttcaagagcgtggtcgctg-3'
  "      HindIII           "

should read
  Bar2f:
  5'-ggagaagcttggcttcaagagcgtggtcgctg-3' (SEQ ID NO: 8)
  --      HindIII           --

Lines 50-52,
  Bar3r:
  5'-catgccatggtcaaatctcggtgacgggcaggacc-3'
  "      NcoI           "

should read
  Bar3r:
  5'-catgccatggtcaaatctcggtgacgggcaggacc-3' (SEQ ID NO: 9)
  --      NcoI           --

Columns 15-Column 16, (Lines 62-65) and Columns 17 - Column 18, (Lines 1-4):
  XbaI
  tctagacttatcgggtgacaaaagttatcaggcatgcacctggtagctagtctttaaaccaatagattgcatcggtttaaaaggcaaga
  ccgtcaaattgcgggaaaggggtcaacagccgttcagtaccaagtctcagggggaaactttgagatggccttgcaaagggtatggtaa
  taagctgacggacatggtcctaaccacgcagccaagtcctaagtcaacagatcttctgttgatatggatgcagttcacagactaaatgt
  cggtcggggaagatgtattcttctcataagatatagtcggacctctccttaatgggagctagcggatgaagtgatgcaacactggagcc
  gctgggaactaatttgtatgcgaaagtatattgattagttttggagtactcgtgataagctt
  "                                    HindIII                "

should read
  XbaI
  tctagacttatcgggtgacaaaagttatcaggcatgcacctggtagctagtctttaaaccaatagattgcatcggtttaaaaggcaaga
  ccgtcaaattgcgggaaaggggtcaacagccgttcagtaccaagtctcagggggaaactttgagatggccttgcaaagggtatggtaa
  taagctgacggacatggtcctaaccacgcagccaagtcctaagtcaacagatcttctgttgatatggatgcagttcacagactaaatgt
  cggtcggggaagatgtattcttctcataagatatagtcggacctctccttaatgggagctagcggatgaagtgatgcaacactggagcc
  gctgggaactaatttgtatgcgaaagtatattgattagttttggagtactcgtgataagctt (SEQ ID NO: 10)
  --                                    HindIII                --

Column 17,

Lines 37-42,

" 5'-ctgaactcac cgcgacgtct gtcgagaagt ttctgatcga aaagttcgac agcgtctccg acctgatgca gctctcggag ggcgaagaat ctcgtgcttt cagcttcgat gtaggagggc gtggatatgt cctgcgggta aatagctgcg ccgatggttt ctacaaagat cgttatgttt-3' "

should read

-- 5'-ctgaactcac cgcgacgtct gtcgagaagt ttctgatcga aaagttcgac agcgtctccg acctgatgca gctctcggag ggcgaagaat ctcgtgcttt cagcttcgat gtaggagggc gtggatatgt cctgcgggta aatagctgcg ccgatggttt ctacaaagat cgttatgttt-3' (SEQ ID NO: 11) --

Column 28,

Line 46, "multi-cellular plant" should read --multi-cellular plant organism--.